United States Patent
Johnson et al.

(10) Patent No.: US 11,839,190 B2
(45) Date of Patent: Dec. 12, 2023

(54) MAIZE VARIETY '166-048'

(71) Applicant: FBN Inputs, LLC, San Carlos, CA (US)

(72) Inventors: Scott S. Johnson, Ames, IA (US); Fredrich M. Wilz, Ankeny, IA (US)

(73) Assignee: FBN Inputs, LLC, San Carlos, CA (US)

( * ) Notice: Subject to any disclaimer, the term of this patent is extended or adjusted under 35 U.S.C. 154(b) by 100 days.

(21) Appl. No.: 17/500,457

(22) Filed: Oct. 13, 2021

(65) Prior Publication Data

US 2022/0117185 A1    Apr. 21, 2022

Related U.S. Application Data

(60) Provisional application No. 63/092,275, filed on Oct. 15, 2020.

(51) Int. Cl.
*A01H 5/10* (2018.01)
*A01H 6/46* (2018.01)

(52) U.S. Cl.
CPC ............ *A01H 6/4684* (2018.05); *A01H 5/10* (2013.01)

(58) Field of Classification Search
None
See application file for complete search history.

(56) References Cited

U.S. PATENT DOCUMENTS 9,241,464 B1 *    1/2016    Garcia ................ A01H 6/4684

* cited by examiner

*Primary Examiner* — Medina A Ibrahim
(74) *Attorney, Agent, or Firm* — KLARQUIST SPARKMAN, LLP

(57) ABSTRACT

Herein provided is a new corn variety designated '166-048' as well as the seeds, plants, plant parts, and derivatives of the new corn variety '166-048'. Also provided are tissue cultures of the new corn variety '166-048' and the plants regenerated therefrom. Methods for producing corn plants by crossing the new corn variety '166-048' with itself or another corn variety and plants produced by such methods are also provided. Hybrids of '166-048' exhibit higher yields and lower harvest moistures than comparable hybrids, and '166-048' has broad general combining ability with Iowa Stiff Stalk Synthetic (BSSS) inbreds.

43 Claims, 5 Drawing Sheets

MAIZE VARIETY '166-048'

CROSS REFERENCE TO RELATED APPLICATION

This application claims the benefit of U.S. Provisional Application No. 63/092,275, filed Oct. 15, 2020. The provisional application is incorporated herein in its entirety.

FIELD

This disclosure provides a new and distinctive maize variety, '166-048'.

BACKGROUND

A goal of hybrid maize (Zea mays) development is to combine, in a single hybrid plant, multiple desirable traits, such as pest resistance, pesticide resistance, heat and/or cold tolerance, drought and/or salinity tolerance, increased yield, improved kernel quality, reduced lodging, better overall agronomic quality, and uniformity in time to crop maturity, germination time, stand establishment, growth rate, and kernel/cob size. Development of superior corn plant hybrids requires production of homozygous inbred plants, crosses of the inbred plants, and evaluation of the crosses. Breeding methods combine the genetic backgrounds of two or more inbred corn plants into pools from which new homozygous inbred plants are produced using selfing and phenotypic or genotypic selection. The resultant hybrid plants are then evaluated for commercial potential.

North American farmers plant tens of millions of acres of corn annually. Global yearly corn production exceeds one billion metric tons. As corn production and consumption continue to rise worldwide, so does the need for reliable hybrid plants bearing various combinations of desirable traits.

SUMMARY

The present disclosure relates to a new maize variety, '166-048'. Maize (Zea mays) is commonly referred to as corn. Hybrids of this new variety show higher yields and lower harvest moisture levels than comparable hybrids (such as '81-025' hybrids), along with broad general combining ability with Iowa Stiff Stalk Synthetic (BSSS) inbreds.

A deposit of the new corn variety '166-048' was made with the American Type Culture Collection (ATCC), 10801 University Blvd., Manassas, VA, 20110. The date of deposit is May 16, 2023. The deposit is intended to meet all of the requirements of 37 C.F.R. §§ 1.801-1.809. The accession number for those deposited seeds of the new corn variety '166-048' is ATCC Accession No: PTA-127596. The deposit will be maintained in the depository for a period of 30 years, or 5 years after the last request, or for the effective life of the patent, whichever is longer, and will be replaced if necessary during that period. In one embodiment, the disclosure provides corn seed deposited as ATCC Accession No: PTA-127596, as well as bulk corn seed containing such seeds.

The disclosure provides corn plants having or consisting of the morphological and physiological characteristics of '166-048', such as the characteristics noted in Tables 7-10, for example, the phenotypic and morphological characteristics provided in Tables 7-9 and, following hybridization, higher yields and lower harvest moisture levels than comparable hybrids. Also provided are seeds of such plants, progeny of such plants, and parts of such plants (such as pollen, ovules, and cells). In one example, the disclosure provides corn plants having the genotype of '166-048'. For example, the disclosure provides plants produced by growing the seed of the new corn variety '166-048'.

The disclosure provides a tissue culture of regenerable cells of the new corn variety '166-048', as well as plants regenerated therefrom. Such regenerated corn plants can include or consist of the physiological and morphological characteristics of a plant grown from the seed of the new corn variety '166-048'. Exemplary regenerable cells include but are not limited to those from protoplasts or cells, such as those from embryos, meristematic cells, pollen, leaves, roots, root tips, anthers, pistils, silk, flowers, kernels, ears, cobs, husks, seed, cotyledons, hypocotyls, shoots, or stems of the new corn variety '166-048'.

Also provided are compositions that include '166-048' seed comprised in plant seed growth media, such as a soil or a synthetic cultivation medium.

The disclosed '166-048' plants and seeds can further include a transgene, such as a transgene introduced by backcrossing or genetic transformation into corn variety '166-048'. In some examples, the transgene confers one or more of herbicide tolerance (or resistance), resistance to a bacterial disease, resistance to a viral disease, resistance to an insect, resistance to a fungal disease, resistance to a nematode, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, waxy starch, modified phytic acid metabolism, modified protein metabolism, water stress resistance, restoration of male fertility, altered starch, thermotolerant amylase, and modified corn fiber characteristics.

The disclosed '166-048' plants and seeds can further include a single locus conversion. For example, provided is a corn plant that includes a single locus conversion introduced by backcrossing or genetic transformation into corn variety '166-048'. Also provided is corn seed that includes a single locus conversion introduced by backcrossing or genetic transformation into corn variety '166-048', and obtaining seed therefrom. In some examples, the a single locus conversion confers one or more of herbicide tolerance (or resistance), resistance to a bacterial disease, resistance to a viral disease, resistance to a fungal disease, resistance to an insect, resistance to a nematode, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, waxy starch, modified phytic acid metabolism, modified protein metabolism, water stress resistance, restoration of male fertility, altered starch, thermotolerant amylase, and modified corn fiber characteristics.

Methods of producing corn seed from the '166-048' corn plants are provided. In some examples, such methods include crossing '166-048' with itself or a second corn plant and harvesting a resulting corn seed. In a cross, either parent may serve as the male or female. In some examples, the second corn plant has one or more desirable traits, which is/are introduced into (e.g., via transformation) plants and seeds resulting from such a cross. For example, the second plant can be transgenic, wherein the transgene confers the desirable trait(s). Seeds produced by such methods, including $F_1$ hybrid seeds, as well as corn plants or parts thereof (including $F_1$ plants) produced by growing such a seed, are provided. In some examples, the method of crossing includes planting seeds of the new corn variety '166-048', cultivating corn plants resulting from the seeds until the plants bear flowers, allowing fertilization of the flowers of the plants; and harvesting seeds produced from the plants.

Corn bears both male flowers (tassels) and female flowers (silks) in separate anatomical structures on the same plant. Self-pollination can occur naturally in corn with no manipulation of the flowers. In some examples, the crossing of two corn plants is accomplished using artificial hybridization. In artificial hybridization, the flower used as a female in a cross is manually cross pollinated prior to maturation of pollen from the flower, thereby preventing self-fertilization, i.e., preventing the silks of a plant from being fertilized by any plant of the same variety, including the same plant. Alternatively, the male parts of the flower are emasculated using known methods. Exemplary methods for emasculating the male parts of a corn flower include physical removal of the male parts, use of a cytoplasmic or genetic factor conferring male sterility, and application of a chemical gametocide to the male parts.

Crossing may allow cross-pollination to occur between a first and second parent plant. When the plants are not in pollinating proximity, this is done by placing a bag, for example a paper or glassine bag, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is no longer viable, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Seeds harvested from at least one of the parent corn plants can be grown to produce a corn plant or hybrid corn plant.

Methods are provided for producing a plant derived from corn variety '166-048', which has one or more added traits, as well as plants and seeds generated from such methods. In one example, such a method provides a corn plant having a single locus conversion of the new corn variety '166-048', wherein the corn plant includes or expresses the physiological and morphological characteristics of the new corn variety '166-048' (such as those shown in Tables 7-9). In some embodiments, the single locus conversion can include a dominant or recessive allele. Such methods can include introducing a transgene that confers one or more additional traits into a plant of the new corn variety '166-048' (e.g., via transformation). Exemplary additional traits include herbicide tolerance (or resistance), resistance to an insect, resistance to a bacterial disease, resistance to a viral disease, resistance to a fungal disease, resistance to a nematode, resistance to a pest, male sterility, restoration of male fertility, site-specific recombination, abiotic stress tolerance (such as tolerance to drought, heat, cold, low or high soil pH level, and/or salt), modified phosphorus characteristics, modified antioxidant characteristics, modified essential seed amino acid characteristics, modified fatty acid metabolism, modified carbohydrate metabolism, modified corn fiber characteristics, waxy starch, altered starch, thermotolerant amylase, or other improved nutritional qualities.

Methods of introducing a single locus conversion (such as an additional trait) into the new corn variety '166-048' are provided. In some examples, the methods include (a) crossing a plant of variety '166-048' with a second plant having one or more additional traits to produce $F_1$ progeny plants; (b) selecting $F_1$ progeny plants that have the additional trait to produce selected $F_1$ progeny plants; (c) crossing the selected progeny plants with at least a first plant of variety '166-048' to produce backcross progeny plants; (d) selecting backcross progeny plants that have the additional trait and physiological and morphological characteristics of corn variety '166-048' to produce selected backcross progeny plants; and (e) repeating steps (c) and (d) one or more times in succession to produce selected second or higher backcross progeny plants that include the additional trait and the physiological and morphological characteristics of corn variety '166-048' when grown in the same environmental conditions. In some embodiments, the single locus confers a desirable trait, such as herbicide tolerance (or resistance), resistance to an insect, resistance to a bacterial disease, resistance to a viral disease, resistance to a fungal disease, resistance to a nematode, resistance to a pest, male sterility, restoration of male fertility site-specific recombination, abiotic stress tolerance (such as tolerance to drought, heat, cold, low or high soil pH level, and/or salt), modified phosphorus characteristics, modified antioxidant characteristics, modified essential seed amino acid characteristics, modified fatty acid metabolism, modified carbohydrate metabolism, waxy starch, altered starch, thermotolerant amylase, modified corn fiber characteristics, and/or other improved nutritional qualities. In some examples, the single locus confers the ability to synthesize a protein encoded by a gene located within the single locus.

Methods of producing a corn plant derived from the new corn variety '166-048', such as an inbred corn plant, are provided. In particular examples the method includes (a) preparing a progeny plant derived from the new corn variety '166-048' by crossing a plant of '166-048' with a corn plant of a second variety; and (b) crossing the progeny plant with itself or a second plant to produce a progeny plant of a subsequent generation which is derived from a plant of the new corn variety '166-048'. In some embodiments, the method further includes (c) growing a progeny plant of a subsequent generation from said seed and crossing the progeny plant of a subsequent generation with itself or a second plant; and (d) repeating steps (b) and (c) for at least 2 additional generations (such as at least 3, at least 5, or at least 10 additional generations, such as 2, 3, 4, 5, 6, 7, 8, 9, 10, 11, 12, 13, 14, 15, 16, 17, 18, 19 or 20 additional generations) with sufficient inbreeding to produce an inbred corn plant derived from the new corn variety '166-048'. In other examples, the method includes (a) crossing a corn plant derived from the new corn variety '166-048' with itself or another corn plant to yield additional corn variety '166-048'-derived progeny corn seed; (b) growing the progeny corn seed of (a) under plant growth conditions, to yield additional corn variety '166-048'-derived corn plants; and (c) repeating the crossing and growing steps of (a) and (b) from 0 to 7 times (such as 0 to 4 or 1 to 5 times, such as 0, 1, 2, 3, 4, 5, 6, or 7 times) to generate further corn variety '166-048'-derived corn plants.

Methods are provided for developing a new corn plant using the new '166-048' variety. For example, the methods can include using '166-048' plants or parts thereof as a source of breeding material in plant breeding techniques, such as recurrent selection, mass selection, bulk selection, backcrossing, pedigree breeding, genetic marker-assisted selection, selfing, outcrossing, haploid production, doubled haploid production, and genetic transformation. In some examples, a plant of the new corn variety '166-048' is used as the male or female parent. Such a method can further include (a) crossing a progeny corn plant derived from hybrid corn variety '166-048' with itself or a second plant to produce a seed of a progeny plant of a subsequent generation; (b) growing the progeny plant of the subsequent generation from said seed of the progeny plant of the subsequent generation; and (c) repeating steps (a) and (b) for at least an additional 3-10 generations to produce a progeny corn plant further derived from the corn variety '166-048'.

The disclosure provides a first generation ($F_1$) hybrid corn seed and plants produced by crossing a plant of the new corn variety '166-048' to a second corn plant. In some embodiments, the $F_1$ hybrid corn plant is grown from the hybrid seed produced by crossing the new corn variety '166-048' to a second corn plant. In specific examples, provided is a seed of an $F_1$ hybrid plant produced with the new corn variety '166-048' as one parent, the second generation ($F_2$) hybrid corn plant grown from the seed of the $F_1$ hybrid plant, and the seeds of the $F_2$ hybrid plant.

Methods of producing hybrid corn seeds are also provided. In one example the method includes crossing the new corn variety '166-048' to a second, distinct corn plant which is nonisogenic to the new corn variety '166-048'. In some examples, the method includes cultivating corn plants grown from seeds of the new corn variety '166-048' and cultivating corn plants grown from seeds of a second, distinct corn plant, until the plants bear flowers. A flower on one of the two plants is cross pollinated with the pollen of the other plant, and the seeds resulting from such a cross are harvested.

The disclosure also provides corn plants and parts thereof produced by any of the methods disclosed herein. Thus, provided herein are plants of corn variety '166-048' that further include a single locus conversion, such as one or more additional traits, for example produced by backcrossing or genetic transformation. In some embodiments, the corn plants produced by the disclosed methods include at least two, at least three, at least four, at least five, or at least 10 of the traits of the new corn variety '166-048' as described herein. In some embodiments, the corn plants produced by the disclosed methods include at least two, at least three, at least four, at least five, or at least 10 of the traits of the new corn variety '166-048' (see Tables 7-9).

Methods are also provided for producing a treated '166-048' corn seed.

Methods are also provided for producing a genetic marker profile, which can include extracting nucleic acids from '166-048' corn seed or a plant grown from such seed, and genotyping said nucleic acids, thereby producing a genetic marker profile.

Methods of plant breeding are also provided. In one example, such a method includes isolating nucleic acids from a seed produced by corn variety '1166-048' or a plant grown from the seed, identifying one or more polymorphisms from the isolated nucleic acids, and selecting a plant having one or more polymorphisms, wherein the plant is used in a plant breeding method.

Also provides are methods of producing nucleic acids, wherein the method can include extracting nucleic acids from an F1 corn plant or seed produced by corn plant '166-048'.

Methods of producing a commodity plant product are provided. In some examples the method includes obtaining or supplying a plant of the new corn variety '166-048', or a part thereof, and producing the commodity plant product therefrom. In some examples the method includes growing and harvesting the plant, or a part thereof. Exemplary commodity plant products include but are not limited to a protein concentrate, a protein isolate, corn kernels, grain, starch, corn syrup, corn meal, corn flour, or corn oil.

The foregoing and other objects and features of the disclosure will become more apparent from the following detailed description which proceeds with reference to the accompanying figures.

DETAILED DESCRIPTION

Description of Terms

Figure 1:
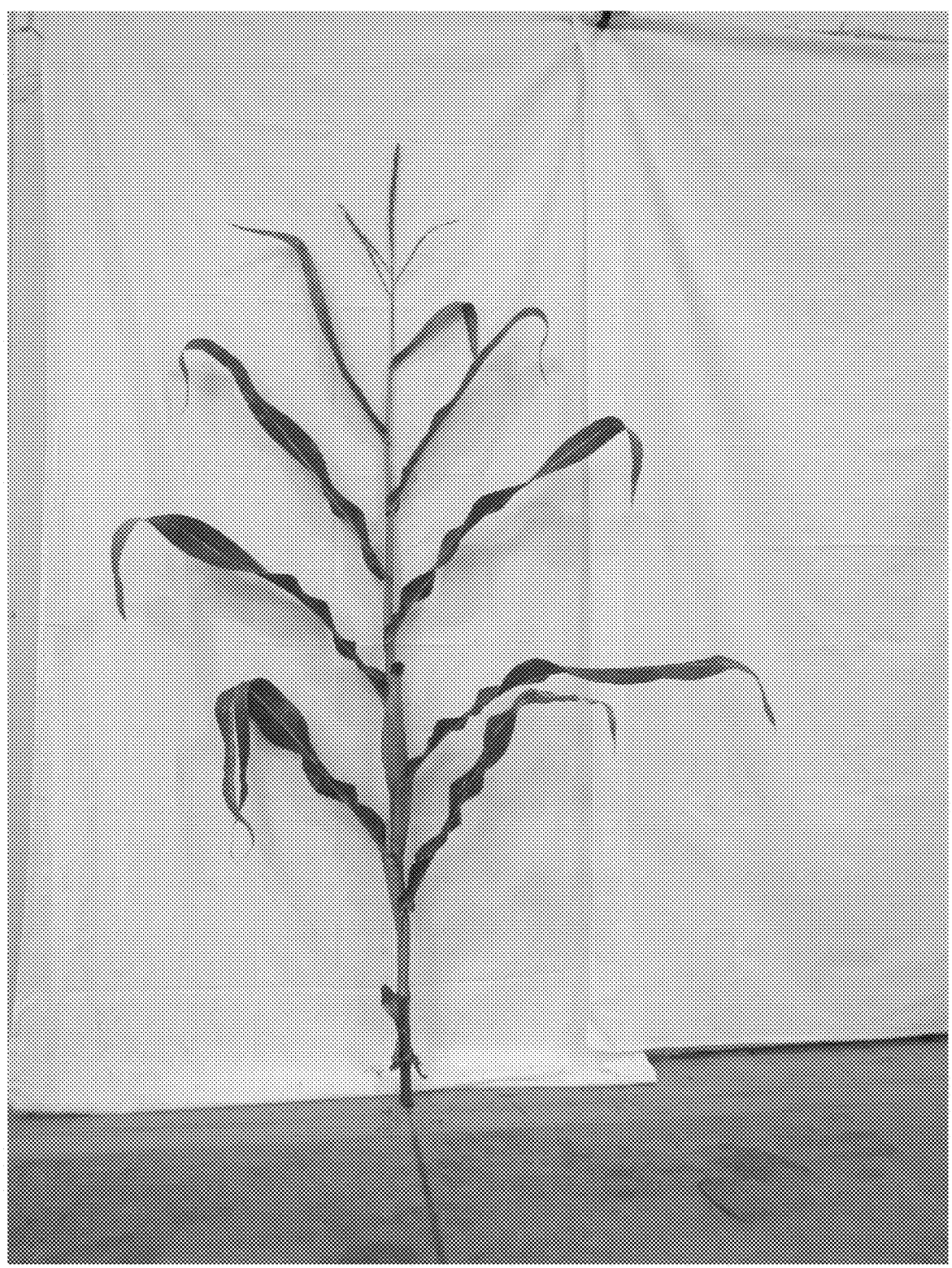
FIG. 1 shows a whole plant of corn variety '166-048'.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps, some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and are not intended to be limiting. All references cited herein are incorporated by reference in their entireties.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment.

Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first generation progeny of the cross of two nonisogenic plants.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Isolated: An "isolated" biological component, such as a nucleic acid, protein or organelle, has been substantially separated or purified away from other biological components in the environment (such as a cell) in which the component occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Lodging: The visual rating of the uprightness of the plants. The score is based on the average of the plants in a plot with a score of 1 to 5, with a score of 1 indicating all plants are erect, and a score of 5 where over about 80% of the plants in a plot are prostrate.

Maturity date: The evaluation of plants considered as mature when about 95% of the pods have reached their mature color.

Moisture (%): The percent moisture of the grain at harvest.

Plant: Includes reference to an immature or mature whole plant, including a plant from which seed, roots or leaves have been removed. Seed or embryo that will produce the plant are also considered to be the plant.

Plant height. Plant height is taken from the top of the soil to the tip of the plant, and is typically measured in centimeters or inches.

Plant parts. Includes protoplasts, leaves, stems, roots, root tips, anthers, pistils, seed, embryo, pollen, ovules, cotyledon, hypocotyl, flower, shoot, tissue, petiole, cells, calli, pods, meristematic cells and the like. Includes plant cells of a tissue culture from which corn plants can be regenerated.

Progeny. Offspring; descendants.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Relative maturity: Refers to the maturity grouping designated by the corn industry over a given growing area. This figure is generally divided into tenths of a relative maturity group. Within narrow comparisons, the difference of a tenth of a relative maturity group equates very roughly to a day difference in maturity at harvest.

Seed. The part of a flowering plant that typically contains the embryo with its protective coat and stored food and that can develop into a new plant under the proper conditions; fertilized and mature ovule.

Seed quality: The visual rating of the completeness of the seed. The score is based on the completeness of the seed coat and overall soundness of the seed. Scores range from 1 to 5, with a score of 1 indicating good quality seed and a score of 5 indicating the seeds are of poor quality.

Seed yield: The yield in bushels/acre (bu/a) and is the actual yield of the grain at harvest, adjusted to 15.5% moisture.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a corn variety are recovered in addition to the characteristics of the single locus transferred into the variety via the backcrossing technique. In particular embodiments, a single locus conversion is generated by genome editing such as through use of engineered nucleases. Examples of engineered nucleases include, but are not limited to, Cas endonucleases, zinc finger nucleases (ZFNs), transcription activator-like effector nucleases (TALENs), and engineered meganucleases, also known as homing endonucleases. Naturally occurring nucleases can also find use for genome editing. In specific embodiments, endonucleases, both naturally occurring and engineered, may utilize any polypeptide-, DNA-, or RNA-guided genome editing systems.

Standability: Calculated as stalk lodging (SL)+root lodging (RL). A lower relative standability value indicates better standability. Stock lodged plants are those that are bent over or broken off below the ear. Root lodged plants are those wherein a portion of the plant leans from the vertical axis by approximately 30 or more degrees.

Tissue culture: A composition that includes isolated cells of the same or a different type or a collection of such cells organized into parts of a plant.

Transformation: The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene: A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a corn plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Corn Having Higher Yield and Lower Harvest Moisture than Comparable Hybrids and Broad General Combining Ability with BSSS Inbreds The present disclosure relates to a new inbred corn variety, '166-048'. Hybrids of this new variety have higher seed yields and lower harvest moisture contents than comparable hybrids, along with broad general combining ability with BSSS inbreds. The new variety is adapted to, for example, areas of North America, such as the United States (such as Iowa, United States), and South America, such as Chile, that commonly grow corn cultivars.

Thus, provided herein is a seed of corn variety '166-048', wherein representative sample seed of the variety was deposited under (ATCC Accession No: PTA-127596). Also provided is bulk corn seed (e.g., a mixture of corn seeds) containing such seeds. Also provided are compositions that include '166-048' seed and plant seed growth media, such as soil or a synthetic cultivation medium. The disclosure provides corn plants having or consisting of the morphological and physiological characteristics of '166-048'. The disclosure also provides corn plants having one or more of (such as at least two, at least three, at least four, at least five, at least 6, at least 7, at least 8, at least 9, or at least 10 of) the morphological and physiological characteristics of '166-048' (such as those listed in Tables 7-9). In one example, such plants have or include the characteristics noted in Table 8, for example green silk color and green stalk brace root color. Also provided are seeds of such plants, progeny of such plants (such as hybrids), parts of such plants (such as pollen, ovules, and cells). In one example, the disclosure provides corn plants having the genotype of '166-048'. For example, the disclosure provides plants produced by growing the seed of the new corn variety '166-048'.

Hybrids of the disclosed '166-048' plants have higher seed yields and lower harvest moisture levels as compared to at least one other corn variety, such as '81-025'. For example, in direct hybrid comparisons, disclosed '166-048' has a higher yield and a lower harvest moisture level as compared to similar '81-025' hybrids (i.e., when both inbreds are crossed to the same inbred) (Table 10).

The disclosed '166-048' plants and seeds can be used to produce other corn plants and seeds, for example as part of a breeding program. Choice of breeding or selection methods using to generate new corn plants and seeds can depend on the mode of plant reproduction, the heritability of the trait(s) being improved, and the type of variety used commercially (e.g., $F_1$ hybrid variety, inbred variety, etc.). For highly heritable traits, a choice of superior individual plants evaluated at a single location can be effective, whereas for traits with low heritability, selection can be based on mean values obtained from replicated evaluations of families of related plants. Exemplary selection methods commonly include pedigree selection, modified pedigree selection, mass selection, recurrent selection, and backcrossing.

The complexity of inheritance influences choice of the breeding method. Backcross breeding can be used to transfer one or a few favorable genes for a highly heritable trait into a desirable variety. This approach has been used extensively for breeding disease-resistant varieties (e.g., see Bowers et al., 1992. *Crop Sci.* 32(1):67-72; Nickell and Bernard, 1992. *Crop Sci.* 32(3):835). Various recurrent selection techniques can be used to improve quantitatively inherited traits controlled by numerous genes.

Promising advanced breeding lines can be thoroughly tested and compared to appropriate standards in environments representative of the commercial target area(s), such as for three or more years. The best or most preferred lines are candidates for new commercial varieties. Those still deficient in certain traits may be used as parents to produce new populations for further selection.

A difficult task is the identification of individuals that are genetically superior, because for many traits the true genotypic value can be masked by other confounding plant traits or environmental factors. One method of identifying a superior plant is to observe its performance relative to other experimental plants and to one or more widely grown standard (such as commercially grown) varieties. Single observations can be generally inconclusive, while replicated observations provide a better estimate of genetic worth.

Plant breeding can result in new, unique and superior corn varieties and hybrids from '166-048'. Two or more parental lines can be selected (such as '166-048' as one of the lines), followed by repeated selfing and selection, producing many new genetic combinations. Each year, the germplasm to advance to the next generation is selected. This germplasm is grown under unique and different geographical, climatic, and soil conditions, and further selections are then made, during and at the end of the growing season. The varieties developed can be unpredictable, because the selection occurs in unique environments, with no control at the DNA level (using conventional breeding procedures), and with millions of different possible genetic combinations being generated.

The development of new corn varieties from '166-048' involves the development and selection of corn varieties, the crossing of these varieties, and selection of progeny from the superior hybrid crosses. A hybrid seed is produced by manual crosses between selected male-fertile parents or by using male sterility systems. Hybrids can be identified using certain single locus traits that indicate that the seed is truly a hybrid. A genetic locus conferring the traits may or may not be transgenic. Examples of such traits include, but are not limited to, male sterility, waxy starch, altered starch, thermotolerant amylase, herbicide resistance, resistance to bacterial, fungal, or viral disease, insect resistance, male fertility, restoration of male fertility, and enhanced nutritional quality. These genes are generally inherited through the nucleus but may be inherited through the cytoplasm. Some known exceptions to this are genes for male sterility, some of which are inherited cytoplasmically, but still act as a single locus trait. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is '166-048') which possess favorable, complementary traits are crossed to produce an $F_1$. An F2 population is produced by selfing one or several $F_1$s, such as an $F_1$ having a low harvest moisture level. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (e.g., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent (e.g., '166-048'). The source of the trait to be transferred is called the donor or nonrecurrent parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population may decline each generation due to failure of some seeds to germinate or some plants to produce at least one seed. As a result, not all of the $F_2$ plants originally sampled in the population are represented by a progeny when generation advance is completed.

In a multiple-seed procedure, one or more ears from each corn plant in a population are commonly harvested and threshed together to form a bulk. Part of the bulk is used to plant the next generation and part is put in reserve. The procedure has also been referred to as modified single-seed descent. The multiple-seed procedure has been used to save labor at harvest. It is considerably faster to thresh (shell) using a machine than to remove one seed from each cob by hand for the single-seed procedure. The multiple-seed procedure also makes it possible to plant the same number of seeds of a population each generation of inbreeding. Sufficient numbers of seeds are harvested to make up for those plants that did not germinate or produce seed.

Descriptions of other breeding methods commonly used for different traits and crops can be found in one of several reference books (e.g., Allard. 1960. Principles of plant breeding. Davis, Calif.: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987. "Principles of variety development." Theory and Technique (Vol. 1)).

Breeding Corn Variety '166-048'

Methods for crossing the new corn variety '166-048' with itself or a second plant are provided, as are the seeds and plants produced by such methods, including $F_1$ and $F_2$ plants and seeds. Such methods can be used for propagation of the new corn variety '166-048', or can be used to produce hybrid corn seeds and the plants grown therefrom. Hybrid corn plants can be used, for example, in the commercial production of corn products or in breeding programs for the production of novel corn varieties. A hybrid plant can also be used as a recurrent parent at any given stage in a backcrossing protocol during the production of a single locus conversion (for example introduction of one or more desirable traits) of the new corn variety '166-048'.

Methods of producing corn plants and/or seed are provided. Such a method can include crossing the new corn variety '166-048' with itself or a second corn plant and harvesting a resulting corn seed, such as an $F_1$ hybrid seed. The resulting plant can be grown, resulting in an $F_1$ corn plant or part thereof.

In one example methods of producing an inbred corn plant derived from corn variety '166-048' are provided. In one example such methods include (a) preparing a progeny plant derived from corn variety '166-048' by crossing a plant of corn variety '166-048' with a corn plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional generation (such as at least 2, at least 3, at least 4, at least 5, at least 6, at least 7, at least 8 at least 9, at least 10, at least 15 or at least 20, such as 2 to 10, 3 to 10, or 3 to 15 generations, such as 2, 3, 4, 5, 6, 7, 8, 9, 10, 15, 20, or 30 generations) with sufficient inbreeding to produce an inbred corn plant derived from the corn variety '166-048'.

The second plant crossed with the new corn variety '166-048' for the purpose of developing novel corn varieties is typically a plant which either itself exhibits one or more additional characteristics or which exhibits one or more additional characteristic(s) when in hybrid combination. In one example, the second corn plant is transgenic. Exemplary additional characteristics include, but are not limited to: increased seed yield, reduced harvest moisture content, lodging resistance, emergence, increased seedling vigor, modified maturity date, desired plant height, high oil content, high protein content, herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to one or more other pests, male sterility, restoration of male fertility, site-specific recombination, other abiotic stress tolerance, modified phosphorus characteristics, modified antioxidant characteristics, modified essential seed amino acid characteristics, modified fatty acid metabolism, modified carbohydrate metabolism, altered starch, thermotolerant amylase, and modified corn fiber characteristics.

When the new corn variety '166-048' is crossed with another different variety, first generation ($F_1$) corn progeny are produced. The hybrid progeny are produced regardless of characteristics of the two varieties crossed. As such, an $F_1$ hybrid corn plant can be produced by crossing '166-048' with any second corn plant. The second corn plant can be genetically homogeneous (e.g., inbred) or can itself be a hybrid. Therefore, the disclosure provides any $F_1$ hybrid corn plant produced by crossing the new corn variety '166-048' with a second corn plant (such as a transgenic plant having one or more genes that confer to the plant one or more additional characteristics).

Corn plants can be crossed by either natural or mechanical techniques (see, e.g., Fehr. 1980. "Corn." In: Hybridization of Crop Plants. Fehr and Hadley (eds). Madison, Wis.: *Am. Soc. Agron., Crop Sci. Soc. Am.*, Chapter 19). Natural pollination occurs in corn either by self-pollination or natural cross pollination, which typically is aided by wind, such as when the wind blows pollen from the tassels to the silks that protrude from the tops of the recipient ears. Mechanical pollination can be accomplished either by controlling the types of pollen that can blow onto the silks or by pollinating by hand. In either natural or artificial crosses, flowering time can be a consideration.

In one embodiment, crossing comprises the steps of: (a) planting in pollinating proximity seeds of a first and a second parent corn plant, and preferably, seeds of a first inbred corn plant and a second, distinct inbred corn plant; (b) cultivating or growing the seeds of the first and second parent corn plants into plants that bear flowers; (c) emasculating flowers of either the first or second parent corn plant, i.e., treating the flowers so as to prevent pollen production, or alternatively, using as the female parent a male sterile plant, thereby providing an emasculated parent corn plant; (d) allowing natural cross-pollination to occur between the first and second parent corn plants; (e) harvesting seeds produced on the emasculated parent corn plant; and, when desired, (f) growing the harvested seed into a corn plant, for example, a hybrid corn plant.

Parental plants are typically planted in pollinating proximity to each other by planting the parental plants in alternating rows, in blocks or in any other convenient planting pattern. When the parental plants differ in timing of sexual maturity, it may be desired to plant the slower maturing plant first, thereby ensuring the availability of pollen from the male parent during the time at which silks on the female parent are receptive to pollen. Plants of both parents are cultivated and allowed to grow until the time of flowering. During this growth stage, plants may be treated with fertilizer and/or other agricultural chemicals as considered advantageous or otherwise appropriate by the grower.

At the time of flowering, in the event that plant '166-048' is employed as the male parent, the tassels of the other parental plant are removed from all plants employed as the female parental plant to avoid self-pollination. The detasseling can be achieved manually but also can be done by machine. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, which is incorporated herein by reference. Furthermore, the use of Roundup herbicide in combination with glyphosate tolerant corn plants to produce male sterile corn plants is disclosed in PCT Publication WO 98/44140.

Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants of the plant being used as the female in the hybridization.

When the plants to be crossed are not in pollinating proximity, cross-pollination may be done by placing a bag, for example a paper or glassine bag, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is no longer viable, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place.

Further, during the hybridization procedure, the parental varieties are grown such that they are isolated from other corn fields to minimize or prevent any accidental contamination of pollen from foreign sources. Such isolation techniques are well known to those of ordinary skill in the art.

Both parental plants may be allowed to continue to grow until maturity or the male rows may be destroyed after flowering is complete. Seeds harvested from at least one of the parent corn plants can be grown to produce a corn plant or hybrid corn plant. Typically, only the ears from the female parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

One use of the instant corn variety is in the production of hybrid seed. Any time the corn plant '166-048' is crossed with a different corn plant, a corn hybrid plant is produced. As such, hybrid corn plant can be produced by crossing '166-048' with any second corn plant. Essentially any other corn plant can be used to produce a corn plant having corn plant '166-048' as one parent. All that is required is that the second plant be fertile, which corn plants naturally are, and that the plant is not corn variety '166-048'. Thus, any corn plant produced using corn plant '166-048' is within the scope of this disclosure. As used herein, crossing can mean selfing, backcrossing, crossing to another or the same variety, crossing to populations, and the like.

The goal of the process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try to combine certain genes within the inbred plants.

The development of new inbred varieties using one or more starting varieties is well known in the art. Novel varieties may be created by crossing a corn variety, followed by multiple generations of breeding according to such well-known methods. New varieties may be created by crossing a corn variety with any second plant. In selecting such a second plant to cross for the purpose of developing novel inbred lines, it may be desired to choose those plants which either themselves exhibit one or more desirable characteristics or which exhibit the desirable characteristic(s) when in hybrid combination. Examples of potentially desirable characteristics include greater yield, reduced harvest moisture content, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and kernel and/or cob size.

Once initial crosses have been made with a corn variety, inbreeding takes place to produce new inbred varieties. Inbreeding requires manipulation by human breeders. Even in the extremely unlikely event inbreeding rather than cross-breeding occurred in natural corn, achievement of complete inbreeding cannot be expected in nature due to well-known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desirable characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection. After at least five generations, the inbred plant is considered genetically pure.

Uniform lines of new varieties may also be developed by way of doubled-haploids. This technique allows the creation of true breeding lines without the need for multiple generations of selfing and selection. In this manner true breeding lines can be produced in as little as one generation. Haploid induction systems have been developed for various plants to produce haploid tissues, plants and seeds. The haploid induction system can produce haploid plants from any genotype by crossing with an inducer line. Inducer lines and methods for obtaining haploid plants are known in the art.

Haploid embryos may be produced, for example, from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Corn has a diploid phase, which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, fewer kernels, and/or weak and/or poor growth, production of inbred plants is an unpredictable and arduous process. Under some conditions, heterozygous advantage at some loci effectively bars perpetuation of homozygosity.

A single cross hybrid corn variety is the cross of two inbred plants, each of which has a genotype which complements the genotype of the other. Typically, $F_1$ hybrids are more vigorous than their inbred parents. This hybrid vigor, or heterosis, is manifested in many polygenic traits, including markedly improved yields, better stalks, better roots, better uniformity, and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D). A three-way cross hybrid is produced from three distinct inbred plants. First, two of those three inbred plants are crossed to generate $F_1$ hybrid progeny. That $F_1$ hybrid progeny is then crossed with the third inbred plant to yield the triple cross hybrid progeny.

Thousands of corn varieties are known to those of skill in the art, any one of which could be crossed with corn plant '166-048' to produce a hybrid plant. Estimates place the number of different corn accessions in gene banks around the world at over 135,000. The Maize Genetics Cooperation Stock Center, which is supported by the U.S. Department of Agriculture, has a total collection of over 100,000 individually pedigreed samples (available at maizecoop.cropsci.uiuc.edu/). When the corn plant '166-048' is crossed with another plant to yield progeny, it can serve as either the maternal or paternal plant. For many crosses, the outcome is the same regardless of the assigned sex of the parental plants.

The development of a hybrid corn variety involves three steps: (1) selecting plants from various germplasm pools; (2) selfing the selected plants for several generations to produce a series of inbred plants, which although different from each other, each breed true and are highly uniform; and (3) crossing the selected inbred plants with unrelated inbred plants to produce $F_1$ hybrid progeny. During this inbreeding process in corn, the vigor of the plants decreases; however, vigor is restored when two unrelated inbred plants are crossed to produce $F_1$ hybrid progeny. An important consequence of the genetic homozygosity and homogeneity of an inbred plant is that the $F_1$ hybrid progeny of any two inbred varieties are genetically and phenotypically uniform. Plant breeders choose these hybrid populations that display phenotypic uniformity. Once the inbred plants that produce superior hybrid progeny have been identified, the uniform traits of their hybrid progeny can be reproduced indefinitely as long as the homogeneity of the inbred parents is maintained.

The development of inbred plants generally requires at least about five to seven generations of selfing. Inbred plants are then crossbred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids.

During the next several years, a progressive elimination of hybrids occurs based on more detailed evaluation of their phenotype. Eventually, trials are conducted to formally compare the experimental hybrids being developed with other hybrids, some of which were previously developed and generally are commercially successful. That is, comparisons of experimental hybrids are made to competitive hybrids to determine if there was any advantage to further development of the experimental hybrids. After comparison testing is complete, determinations may be made whether commercial development should proceed for a given hybrid.

The present disclosure provides a genetic complement of the hybrid corn plant variety designated '166-048'. As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition in which both alleles at a locus are characterized by the same nucleotide sequence or size of a repeated sequence. Heterozygosity refers to different conditions of the gene at a locus. An exemplary type of genetic marker for use with the invention is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

Corn Plants Having One or More Additional Heritable Traits

The disclosure provides plants of the new corn variety '166-048' modified to include one or more additional heritable traits. In some examples, such plants can be developed using backcrossing or genetic engineering (for example by introducing one or more transgenes into the '166-048' variety, wherein the transgenes encode one or more additional traits), wherein essentially all of the morphological and physiological characteristics of the '166-048' variety are recovered in addition to a genetic locus transferred into the plant via the backcrossing technique. Plants developed using such methods can be referred to as a single locus converted plant.

In one example, the method of introducing one or more additional traits into corn variety '166-048' includes (a) crossing a plant of variety '166-048' with a second plant having one or more additional traits to produce $F_1$ progeny plants; (b) selecting $F_1$ progeny plants that have the one or more additional traits to produce selected $F_1$ progeny plants; (c) crossing the selected progeny plants with at least a first plant of variety '166-048' to produce backcross progeny plants; (d) selecting backcross progeny plants that have the one or more additional traits and physiological and morphological characteristics of corn variety '166-048' to produce selected backcross progeny plants; and (e) repeating steps (c) and (d) one or more times in succession to produce selected second or higher backcross progeny plants that have the one or more additional traits and the physiological and morphological characteristics of corn variety '166-048' when grown in the same environmental conditions.

Backcrossing methods can be used to improve or introduce a characteristic into the new corn variety '166-048' (for example using the methods provided in U.S. Pat. No. 10,757,896). The parental corn plant which contributes the locus for the additional characteristic is termed the "nonrecurrent" or "donor" parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Fehr. 1987. "Principles of variety development." In Theory and Technique (Vol. 1) and Crop Species corn (Vol. 2). New York: Macmillan Publishing Company, pp. 360-376; Sprague and Dudley, eds. 1988. Corn and Improvement, 3rd edition). In a typical backcross protocol, the original variety of interest (recurrent parent, e.g., '166-048') is crossed to a second variety (nonrecurrent parent) that carries the single locus of interest (such as a desirable trait) to be transferred. The resulting progeny from this cross are then crossed again to the recurrent parent and the process is repeated until a corn plant is obtained wherein essentially all of the morphological and physiological characteristics of the recurrent parent (e.g., '166-048') are recovered (such as increased yield and reduced harvest moisture content) in the converted plant, in addition to the single transferred locus from the nonrecurrent parent.

The goal of a backcross protocol is to alter or substitute a single trait or characteristic in the original variety, such as '166-048'. To accomplish this, a single locus of the recurrent variety is modified or substituted with the additional locus from the nonrecurrent parent, while retaining essentially all of the rest of the genetic traits, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the additional characteristic has been successfully transferred.

In a backcross where the additional characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield or resistance to a pest. As in this example, lines with the phenotype of the recurrent parent can be composited without the usual replicated tests for traits such as yield, protein or oil percentage in the individual lines.

Corn varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus characteristics, modified antioxidant characteristics, modified essential seed amino acid characteristics, modified fatty acid metabolism, modified carbohydrate metabolism, waxy starch, altered starch, altered starch, thermotolerant amylase, and modified corn fiber characteristics, yield stability, and yield enhancement. These comprise genes generally inherited through the nucleus (with some exceptions inherited cytoplasmically). Thus, plants of corn variety '166-048' that include a single locus conversion (such as one that confers an additional trait) are provided herein.

Direct selection can be applied where the single locus acts as a dominant trait. An example of a dominant trait is the herbicide resistance trait (such as glyphosate tolerance). For the selection process, the progeny of the initial cross are sprayed with an herbicide (such as glyphosate) prior to the backcrossing. The spraying eliminates any plants which do not have the herbicide tolerance characteristic; only those plants which have the herbicide resistance gene are used in the subsequent backcross. This process is then repeated for all additional backcross generations.

Selection of corn plants for breeding may not be dependent on the phenotype of a plant and instead can be based on genetic investigations. For example, a suitable genetic marker can be used which is closely genetically linked to a trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to the breeding of corn are known. Such methods can be useful in the case of recessive traits and variable phenotypes, or where conventional assays are more expensive, time consuming or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858), and Single Nucleotide Polymorphisms (SNPs).

Qualitative characters can be useful as phenotype-based genetic markers in corn; however, some or many may not differ among varieties commonly used as parents. Widely used genetic markers include seedling emergence, kernel sucrose concentration, and kernel tenderness. Differences in maturity, height, hilum color, and pest resistance between parents can also be used to verify hybrid plants.

Useful or desirable traits can be introduced by backcrossing, as well as directly into a plant by genetic transformation methods. Genetic transformation can therefore be used to insert a selected transgene into the '166-048' variety or can, alternatively, be used for the preparation of transgenes which can be introduced by backcrossing. Thus, the disclosure provides methods of producing a plant of corn variety '166-048' that includes one or more added traits, for example that include introducing a transgene(s) conferring the one or more additional traits into a plant of corn variety '166-048' (for example by transformation with a transgene that confers upon the corn plant the additional trait), thereby producing a plant of corn variety '166-048' that includes the one or more added traits.

Methods for the transformation of many economically important plants, including corn, are known. Methods for introducing a nucleic acid molecule (e.g., transgene), such as DNA, RNA, or inhibitory RNAs, are known, and the disclosure is not limited to particular methods. Exemplary techniques which can be employed for the genetic transformation of corn include, but are not limited to, electroporation (U.S. Pat. No. 5,384,253), electrotransformation (U.S. Pat. No. 5,371,003), microprojectile bombardment (U.S. Pat. Nos. 5,550,318, 5,736,369 and 5,538,880; and PCT Publication WO 95/06128), *Agrobacterium*-mediated transformation (U.S. Pat. No. 5,591,616 and European Patent Application Publication No. EP0672752), direct DNA uptake transformation of protoplasts and silicon carbide fiber-mediated transformation (U.S. Pat. Nos. 5,302,532 and 5,464,765).

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner.

Protoplasts can also be employed for electroporation transformation of plants (Bates. 1994. *Mol. Biotechnol.* 2(2):135-145; Lazzeri. 1995. *Methods Mol. Biol.* 49:95-106). For example, the generation of transgenic corn plants by electroporation of cotyledon-derived protoplasts has been described by Dhir and Widholm (WO 1992/017598).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target corn cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large. Microprojectile bombardment methods can be used to transform corn s, as described, for example, in U.S. Pat. No. 5,322,783.

*Agrobacterium*-mediated transfer can be used to introduce gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. *Bio. Tech.* 3(7):629-635; U.S. Pat. No. 5,563,055), and its use for corn transformation has been described (Chee and Slightom. 1995. *Methods Mol. Biol.* 44:101-119; U.S. Pat. No. 5,569,834). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457). The ability to regenerate corn plants from protoplasts makes these techniques applicable to corn (Dhir et al. 1991. *Plant Cell Rep.* 10(2):97-101).

In one example, such methods can also be used to introduce transgenes for the production of proteins in transgenic corn. The resulting produced protein can be harvested from the transgenic corn. The transgene can be harvested from the transgenic plants that are originated or are descended from the new corn variety '166-048', a seed of '166-048' or a hybrid progeny of '166-048'.

Numerous different genes are known and can be introduced into a corn plant '166-048' or progeny thereof. Non-limiting examples of particular genes and corresponding phenotypes that can be chosen for introduction into a corn plant are provided herein.

Included among various plant transformation techniques are methods permitting the site-specific modification of a plant genome. These modifications can include, but are not limited to, site-specific mutations, deletions, insertions, and replacements of nucleotides. These modifications can be made anywhere within the genome of a plant, for example, in genomic elements, including, among others, coding sequences, regulatory elements, and non-coding DNA sequences. Any number of such modifications can be made and the modifications may be made in any order or combination, for example, simultaneously, all together, or one after another. Such methods may be used to modify a particular trait conferred by a locus. Techniques for making such modifications by genome editing are well known in the art and include, for example, use of CRISPR-Cas systems, zinc-finger nucleases (ZFNs), and transcription activator-like effector nucleases (TALENs), among others.

It is understood to those of skill in the art that a transgene need not be directly transformed into a plant, as techniques for the production of stably transformed corn plants that pass single loci to progeny by Mendelian inheritance is well known in the art. Such loci may therefore be passed from parent plant to progeny plants by standard plant breeding techniques that are well known in the art.

Male Sterility

As described herein, the inbred and hybrid plants provided herein can include male sterility. Accordingly, in some examples, sterile hybrids are produced and the pollen necessary for the formation of grain on these hybrids is supplied by interplanting of fertile inbreds in the field with the sterile hybrids. Examples of genes conferring male sterility include those disclosed in U.S. Pat. Nos. 3,861,709, 3,710,511, 4,654,465, 5,625,132, and 4,727,219, each of the disclosures of which are incorporated herein by reference in their entirety. Male sterility genes can increase the efficiency with which hybrids are made, in that they eliminate the need to physically emasculate the corn plant used as a female in a given cross.

When employing a male sterility system with a disclosed corn plant, one or more male-fertility restorer genes may be used. For example, when cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with the result that all of the progeny are male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful when the vegetative tissue of the corn plant is utilized (e.g., for silage), but in most cases, the seeds will be deemed the most valuable portion of the crop, so fertility of the hybrids in these crops must be restored. Therefore, one aspect of the current disclosure concerns the hybrid corn plant '166-048' comprising a genetic locus capable of restoring male fertility in an otherwise male-sterile plant. Examples of male-sterility genes and corresponding restorers which could be employed with the plants provided herein are known and are disclosed in, for example, U.S. Pat. Nos. 5,530,191; 5,689,041; 5,741, 684; and 5,684,242, which are incorporated herein by reference in their entirety.

Additional techniques exist that are designed to avoid detasseling in maize hybrid production. Nonlimiting examples of such techniques include switchable male sterility, lethal genes in the pollen or anther, inducible male sterility and/or male sterility genes with chemical restorers. Additional examples include, but are not limited to, U.S. Pat. No. 6,025,546, which describes the use of tapetum-specific promoters and the barnase gene to produce male sterility, and U.S. Pat. No. 6,627,799, which describes modifying stamen cells to provide male sterility. Therefore, a '164-005>1' or '164-005>2' corn plant can include one or more nucleotide sequences that restore male fertility to male-sterile maize inbreds or hybrids and/or one or more nucleotide sequences or traits to produce male sterility in maize inbreds or hybrids.

Furthermore, methods for genetic male sterility are disclosed in EPO Publication No. 89/3010153.8, PCT Publication No. WO 90/08828 and U.S. Pat. Nos. 4,654,465, 4,727,219, 3,861,709, 5,432,068 and 3,710,511. Gametocides, some of which are taught in U.S. Pat. No. 4,735,649 (incorporated by reference) can be employed to make the plant male sterile. Gametocides, including, but not limited to, glyphosate, and its derivatives are chemicals or substances that negatively affect the pollen or at least the fertility of the pollen and provide male sterility to the seed producing parent.

Inbred seed in a sample of hybrid seed may be detected using molecular markers. Alternatively, the seed sample can be planted and an inbred capture process can be used to isolate inbred seed from the hybrid F1 seed sources. The inbred plants can be distinguished from the hybrid plants due to the inbreds having a stunted appearance, i.e., shorter plant, smaller ear, etc. Self pollination of the stunted plants grown from these identified putative inbred plants produces either the female inbred seed, if it was an inbred plant or if it was a weak hybrid than the hybrid kernel will be F2 seed. The resultant plants can observed for size or they can be tested by markers to identify any inbred plants. The identified inbred plants can be selected and self-pollinated to form the inbred seed.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458). In one non-limiting example, the herbicide resistance gene is a gene that confers resistance to the sulfonylurea herbicide nicosulfuron.

Resistance genes for glyphosate (e.g., resistance conferred by mutant 5-enolpyruvl-3 phosphikimate synthase (EPSPS) enzyme and aroA genes) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSP transformation events conferring glyphosate resistance are described, for example, in U.S. Pat. Nos. 6,040,497 and 7,632,985. The MON89788 event disclosed in U.S. Pat. No. 7,632,985 can be used to confer glyphosate tolerance in combination with an increase in average yield relative to prior events. Exemplary PAT sequences are provided in RE44962.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Genes conferring resistance to an herbicide that inhibits photosynthesis are also known, such as, a triazine (psbA and gs+genes) and a benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseudomonas maltophilia*, which is involved in the conversion of an herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Genes are also known that confer resistance to herbicides that inhibit photosynthesis such as, for example, triazine herbicides (psbA and gs+ genes) and benzonitrile herbicides (nitrilase gene). In one non-limiting example, a gene confers resistance to the benzonitrile herbicide bromoxynil. Przibila et al. (*Plant Cell,* 3:169, 1991) describe the transformation of *Chlamydomonas* with plasmids encoding mutant psbA genes. Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes, et al. (*Biochem. J.,* 285:173, 1992). 4-hydroxyphenylpyruvate dioxygenase (HPPD) is a target of the HPPD-inhibiting herbicides, which deplete plant plastoquinone and vitamin E pools. Rippert, et al. (*Plant Physiol.,* 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt, et al., *PNAS,* 103(33):12329, 2006). The herbicide methyl viologen inhibits $CO_2$ assimilation. Foyer, et al. (*Plant Physiol.,* 109:1047, 1995) describe a plant overexpressing glutathione reductase (GR) that is resistant to methyl viologen treatment.

Siminszky (*Phytochemistry Reviews,* 5:445, 2006) describes plant cytochrome P450-mediated detoxification of multiple, chemically unrelated classes of herbicides. Modified bacterial genes have been successfully demonstrated to confer resistance to atrazine, an herbicide that binds to the plastoquinone-binding membrane protein $Q_B$ in photosystem II to inhibit electron transport. For example, Cheung, et al. (*PNAS,* 85:391, 1988) describe tobacco plants expressing the chloroplast psbA gene from an atrazine-resistant biotype of *Amaranthus hybridus* fused to the regulatory sequences of a nuclear gene, and Wang, et al. (*Plant Biotech. J.,* 3:475, 2005) describe transgenic alfalfa, *Arabidopsis*, and tobacco plants expressing the atzA gene from *Pseudomonas* sp. that were able to detoxify atrazine.

Bayley, et al. (*Theor. Appl. Genet.,* 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a dicamba monooxygenase (DMO) gene from *Pseudomonas maltophilia* that is involved in the conversion of dicamba to a non-toxic 3,6-dichlorosalicylic acid and thus may be used for producing plants tolerant to this herbicide.

Other examples of herbicide resistance have been described, for example, in U.S. Pat. Nos. 6,803,501; 6,448,476; 6,248,876; 6,225,114; 6,107,549; 5,866,775; 5,804,425; 5,633,435; 5,463,175.

Disease Resistance

Plant defenses are often activated by specific interaction between the product of a disease resistance gene (R) in the plant and the product of a corresponding avirulence (Avr) gene in the pathogen. A plant, such as '166-048' or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium fulvum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses (Beachy et al. 1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody can also be used. For example, Tavladoraki et al. (1993. *Nature* 366:469-472) show that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production.

Logemann et al. (1992. *Biotechnology*, 10:305), for example, disclose transgenic plants expressing a barley ribosome-inactivating gene have an increased resistance to fungal disease. Plant defensins may be used to provide resistance to fungal pathogens (Thomma et al., *Planta*, 216:193, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; 6,316,407; and 6,506,962.

Insect Resistance

One example of an insect resistance gene is one that encodes a *Bacillus thuringiensis* (Bt) protein (a Cry toxin), a derivative thereof or a synthetic polypeptide modeled thereon (e.g., Geiser et al., 1986. *Gene* 48:109, discloses a Bt δ-endotoxin gene). Moreover, DNA molecules encoding δ-endotoxin genes can be obtained from the ATCC (Manassas, Va.), for example under ATCC Accession Nos. 40098, 67136, 31995 and 31998. Another example is a lectin. For example, Van Damme et al. (1994. *Plant Mol Biol* 24(5): 825-830) disclose several *Clivia miniata* mannose-binding lectin genes. A vitamin-binding protein can also be used, such as avidin. See WO 1994/000992, which teaches the use of avidin and avidin homologues as larvicides against insect pests. In one example, the *Bacillus thuringiensis* (Bt) protein is a member of the Cry1 class, and is active primarily against larval stages of the order Lepidoptera. Examples include Cry1Ab (Bt11), Cry1Ac, and Cry1F (e.g., Cry1Fa2 (TC1507)), as well as variants and truncations thereof that provide insect resistance. In one example, the *Bacillus thuringiensis* (Bt) protein is a member of the Cry2 class or the Cy3 class (such as Cy34Ab1, Cry35ab1).

In one example the insect resistance gene is an enzyme inhibitor, for example, a protease, proteinase inhibitor, or an α-amylase inhibitor. For example, Abe et al. (1987. *J. Biol. Chem.* 262:16793-7) disclose a rice cysteine proteinase inhibitor, Genbank Accession Nos. Z99173.1 and DQ009797.1 disclose proteinase inhibitor coding sequences, Huub et al. (*Plant Molec. Biol.*, 21:985, 1993) describes the nucleotide sequence of cDNA encoding tobacco proteinase inhibitor I, and Sumitani et al. (1993. *Plant Mol. Biol.* 21:985) discloses the nucleotide sequence of *Streptomyces nitrosporeus* α-amylase inhibitor. An insect-specific hormone or pheromone can also be used. For example, Hammock et al. (1990. *Nature* 344:458-461) disclose juvenile hormone esterase, an inactivator of juvenile hormone.

An insect-specific hormone or pheromone may also be used. For example, Hammock et al. (Nature, 344:458, 1990) describe baculovirus expression of cloned juvenile hormone esterase, an inactivator of juvenile hormone. Further, Gade and Goldsworthy (Eds., Physiological Systems in Insects, Elsevier Academic Press, Burlington, Mass., 2007) describe allostatins and their potential use in pest control, and Palli et al. (*Vitam. Horm.*, 73:59, 2005) describes the use of ecdysteroid and ecdysteroid receptor in agriculture. Additionally, Price et al., (*Insect Mol. Biol.*, 13:469, 2004) identified the diuretic hormone receptor (DHR) as a candidate target of insecticides.

Still other examples include an insect-specific antibody or an immunotoxin derived therefrom and a developmental-arrestive protein. For example, Taylor et al. (1994. Seventh Intl. Symposium on Molecular Plant-Microbe Interactions (Edinburgh Scotland), Abstract #497) describe enzymatic inactivation in transgenic tobacco via production of single-chain antibody fragments.

Nematode resistance has been described, for example, in U.S. Pat. No. 6,228,992, and bacterial disease resistance has been described, for example, in U.S. Pat. No. 5,516,671.

Modified Fatty Acid, Phytate and Carbohydrate Metabolism

Genes conferring modified fatty acid metabolism can be introduced into '166-048' and its progeny, such as antisense stearoyl acyl carrier protein (ACP) desaturase genes (EC 1.14.99.6) (e.g., Knutzon et al. 1992. *PNAS* 89:2624-2628). Fatty acid desaturases can be introduced into '166-048' and its progeny, such as *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992. *J Biol Chem* 267(9):5931-5936); a gene encoding a stearoyl-acyl carrier protein –9 desaturase from castor (Fox et al. 1993. *PNAS* 90(6):2486-2490); Δ6- and Δ12-desaturases from the cyanobacteria *Synechocystis* responsible for the conversion of linoleic acid (18:2) to gamma-linolenic acid (18:3 gamma) (Reddy et al., 1993. *Plant Mol Biol* 22(2):293-300); a gene from *Arabidopsis thaliana* that encodes an omega-3 desaturase (Arondel et al. 1992. *Science* 258:1353-5); plant Δ9-desaturases (WIPO Publication No. WO 1991/013972) and corn and *Brassica* Δ15 desaturases (European Patent Application Publ. No. EP 0616644).

Phytate metabolism can also be modified by introduction of a phytase-encoding gene to enhance breakdown of phytate, adding more free phosphate to the transformed plant. For example, see Van Hartingsveldt et al. (1993. *Gene* 127:87-94), for an *Aspergillus niger* phytase gene. In corn, this, for example, could be accomplished by cloning and then reintroducing DNA associated with the single allele which is responsible for corn mutants characterized by low levels of phytic acid. See Raboy et al. (2000, *Plant Physiol.* 124(1):355-68).

A number of genes are known that can be used to alter carbohydrate metabolism. For example, plants can be transformed with a gene coding for an enzyme that alters the branching pattern of starch. See Shiroza et al. (1988. *J Bacteriol* 170(2):810-816) (*Streptococcus* fructosyltransferase gene), Steinmetz et al. (1985. Mol Gen Genet. 200:220-228) (*Bacillus subtilis* levansucrase gene), Pen et al. (1992. *BioTechnology* 10:292) (*Bacillus lichenifonnis* α-amylase), Elliot et al. (1993. *Plant Mol. Biol* 21:515) (tomato invertase genes), Sergaard et al. (1993. *J. Biol. Chem.* 268:22480) (site-directed mutagenesis of barley α-amylase gene), and Fisher et al. (1993. *Plant Physiol* 102:1045) (maize endosperm starch branching enzyme II). The Z10 gene encoding a 10 kD zein storage protein from maize can also be used to alter the quantities of 10 kD zein in the cells relative to other components (Kirihara et al., 1988. *Mol Gen Genet.* 211:477-484).

U.S. Pat. No. 6,930,225 describes corn cellulose synthase genes and methods of use thereof.

Resistance to Abiotic Stress

Abiotic stress tolerance in '166-048' or in progeny of '166-048' can include, but is not limited to, tolerance to stress induced by, for example, flowering, ear and seed development, enhancement of nitrogen utilization efficiency, altered nitrogen responsiveness, drought resistance or tolerance, cold resistance or tolerance, heat resistance or tolerance, low or high soil pH level resistance or tolerance, submergence tolerance, tolerance of exposure to heavy metals, oxidative stress tolerance, and salt resistance or tolerance. Such abiotic stress tolerance can increase yield under stress.

Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878.

Additional Traits

Additional traits can be introduced into the disclosed corn variety or progeny of the disclosed variety. A non-limiting example of such a trait is a coding sequence that decreases RNA and/or protein levels. The decreased RNA and/or protein levels may be achieved through RNAi methods, such as those described in U.S. Pat. No. 6,506,559.

Modifications can also include site-specific recombination; modified antioxidant characteristics; modified essential seed amino acid characteristics, or the like, or any combination thereof. Merely by way of example, FRT sites and/or Lox sites can be introduced into a corn plant. FRT sites can be used in the FLP/FRT system. Lox sites can be used in the Cre/Loxp system. Modifications can be made to a corn plant to introduce modified antioxidant characteristics (e.g., content or composition, such as alteration of tocopherol or tocotrienols) and/or modified essential seed amino acid characteristics (e.g., increasing accumulation of essential amino acids in seeds). Exemplary useful genes and traits for transgenic modification of the variety are disclosed in, for example, U.S. Pat. Nos. 7,687,686, 7,649,127 and 7,645,923.

In addition to the modification of oil, fatty acid, or phytate content described above, it may additionally be beneficial to modify the amounts or levels of other compounds. For example, the amount or composition of antioxidants can be altered. For example, U.S. Pat. Nos. 6,787,618 and 7,154,029 and International Patent Application Publication No. WO 00/68393 disclose manipulation of antioxidant levels, and International Patent Application Publication No. WO 03/082899 discloses manipulation of an antioxidant biosynthetic pathway.

Additionally, seed amino acid content may be manipulated. U.S. Pat. No. 5,850,016 and International Patent Application Publication No. WO 99/40209 disclose alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent Application Publication No. WO 99/29882 discloses methods for altering amino acid content of proteins. International Patent Application Publication No. WO 98/20133 describes proteins with enhanced levels of essential amino acids. International Patent Application Publication No. WO 98/56935 and U.S. Pat. Nos. 6,346,403, 6,441,274, and 6,664,445 disclose plant amino acid biosynthetic enzymes. International Patent Application Publication No. WO 98/45458 describes synthetic seed proteins having a higher percentage of essential amino acids than wildtype.

U.S. Pat. No. 5,633,436 discloses plants comprising a higher content of sulfur-containing amino acids; U.S. Pat. No. 5,885,801 discloses plants comprising a high threonine content; U.S. Pat. No. 5,885,802 discloses plants comprising a high methionine content; U.S. Pat. No. 5,912,414 discloses plants comprising a high methionine content; U.S. Pat. No. 5,990,389 discloses plants comprising a high lysine content; U.S. Pat. No. 6,459,019 discloses plants comprising an increased lysine and threonine content; International Patent Application Publication No. WO 98/42831 discloses plants comprising a high lysine content; International Patent Application Publication No. WO 96/01905 discloses plants comprising a high threonine content; and International Patent Application Publication No. WO 95/15392 discloses plants comprising a high lysine content.

Tissue Cultures and In Vitro Regeneration of Corn Plants

Tissue cultures of the new corn variety '166-048' are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, kernels, ears, cobs, leaves, husks, stalks, roots, root tips, anthers, silk, and the like. In a particular example, the tissue culture includes embryos, protoplasts, meristematic cells, pollen, leaves or anthers of the new corn variety '166-048'. Also provided are corn plants regenerated from such tissue cultures, wherein the regenerated corn plant expresses the physiological and morphological characteristics of the corn variety '166-048'. Means for preparing and maintaining plant tissue cultures are well known in the art (U.S. Pat. Nos. 5,538,880 and 5,550,318, which ae incorporated herein by reference). By way of example, a tissue culture comprising organs such as tassels or anthers has been used to produce regenerated plants (U.S. Pat. Nos. 5,445,961 and 5,322,789, which are incorporated herein by reference).

One type of tissue culture is tassel/anther culture. Tassels contain anthers which in turn enclose microspores. Microspores develop into pollen. For anther/microspore culture, if tassels are the plant composition, they can be selected at a stage when the microspores are uninucleate, that is, include only 1, rather than 2 or 3 nuclei. Methods to determine the correct stage are well known to those skilled in the art and include mitramycin fluorescent staining, trypan blue, and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4° C. to 25° C. may be preferred, and a range of 8° C. to 14° C. may be particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are disclosed in, for example, U.S. Pat. Nos. 5,322,789 and 5,445,961, which are incorporated herein by reference.

Although not required, when tassels are employed as the plant organ, it is generally beneficial to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When tassels are employed directly, tassels are generally pretreated at a cold temperature for a predefined time, often at 10° C. for about four days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol, sorbitol, inositol, or the like. An exemplary synergistic combination is the use of mannitol at a temperature of about 10° C. for a period ranging from about 10 to 14 days. In one embodiment, 3 ml of 0.3M mannitol combined with 50 mg/l of ascorbic acid, silver nitrate, and colchicine is used for incubation of anthers at 10° C. for between 10 and 14 days. Another embodiment is to substitute sorbitol for mannitol. The colchicine produces chromosome doubling at this early stage. The chromosome doubling agent is generally only present at the preculture stage.

It is believed that the mannitol or other similar carbon structures or environmental stress induce starvation and function to force microspores to focus their energies on entering developmental stages. The cells are unable to use, for example, mannitol as a carbon source at this stage. It is believed that these treatments cause the cells to develop as embryoids and plants from microspores. Dramatic increases in development from these haploid cells, as high as 25 embryoids in $10^4$ microspores, have resulted from using these methods.

To isolate microspores, an isolation media is generally used. An isolation media is used to separate microspores from the anther walls while maintaining their viability and embryogenic potential. An exemplary embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l $AgNO_3$. In another embodiment, the biotin and proline are omitted.

An isolation media preferably has a higher antioxidant level when it is used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably, from about 50 mg/l to about 100 mg/l.

It is beneficial to provide a support for the microspores during culturing and subculturing. Any support that maintains the cells near the surface can be used. An exemplary embodiment of a solid support is a TRANSWELL® culture dish. Another embodiment of a solid support for development of the microspores is a bilayer plate wherein liquid media is on top of a solid base. Other embodiments include a mesh or a millipore filter. A solid support may be a nylon mesh in the shape of a raft. A raft is defined as an approximately circular support material that is capable of floating slightly above the bottom of a tissue culture vessel, for example, a petri dish, of about 60 or 100 mm in size, although any other laboratory tissue culture vessel will suffice. In an exemplary embodiment, a raft is about 55 mm in diameter.

Culturing isolated micro spores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, GELRITE™ (solidifying agent). The liquid medium passes through the mesh while the microspores are retained and supported at the medium-air interface. The surface tension of the liquid medium in the petri dish causes the raft to float. The liquid is able to pass through the mesh; consequently, the microspores stay on top. The mesh remains on top of the total volume of liquid medium.

The exemplary culture vessels can be further defined as either (1) a bilayer 60 mm petri plate wherein the bottom 2 ml of medium are solidified with 0.7% agarose overlaid with 1 mm of liquid containing the microspores; (2) a nylon mesh raft wherein a wafer of nylon is floated on 1.2 ml of medium and 1 ml of isolated microspores is pipetted on top; or (3) TRANSWELL® plates wherein isolated microspores are pipetted onto membrane inserts which support the microspores at the surface of 2 ml of medium.

Examples of processes of tissue culturing and regeneration of corn are described in, for example, European Patent Application Publication No. EP0160390, PCT Application WO 95/06128, and U.S. Pat. No. 5,736,369.

Embryogenic cultures can also be used for regeneration, including regeneration of transgenic plants.

Example 1

Breeding History of '166-048'

The development of corn variety '166-048' was begun in 2012, when corn variety '81-025' was crossed to '87-329' in a nursery near Kelley, IA. Both '81-025' and '87-329' are proprietary corn inbreds; they were derived from various non-BSSS sources. The general genetic background of '81-025' is Oh43/LH82/BSCB1/tropical; the general genetic background of '87-329' is BSCB1/tropical/LH123/LH59. The breeding history of '166-048' is provided in Table 1.

TABLE 1

Breeding history of '166-048'.

| NURSERY PROGRAM | NURS row | NURS location | seed row | | male | action | RESULTING LINE CODE |
|---|---|---|---|---|---|---|---|
| 2012.IA.MISC (Block 2) | 12s.01359 | near Kelley, IA | 87-329 | x | 81-025 | cross | |
| 2012-13.WN.JEG (Block 8) | 12w.08032 | near Buin, CHILE | 87-329 x 81-025 | x | SELF | bulk 10 selfs | |
| 2013.IA.POPNS (Block 1) | 13s.00021 | near Kelley, IA | (87-329x81-025)@1 | x | SELF | select 1 self | 13A.166c-048 |
| 2013-14.WN.JEG (Block 2) | 13w.01596 | near Buin, CHILE | 13A.166c-048 | x | SELF | bulk 2 selfs | 13A.166c-048-B |
| 2014.IA.ECQUAD (Seg4 Block) not in 2014-15 WN | 14s.07721 | near Kelley, IA | 13A.166c-048-B | x | SELF | bulk 2 selfs | 13A.166c-048-B-B |
| 2015.IA.INTERM not in 2015-16 WN | 15s.11553 | near Kelley, IA | 13A.166c-048-B-B | x | SELF | select 1 self | 13A.166c-048-B-B-2 |
| 2016.IA.SegAS | 16s.05850 | near Kelley, IA | 13A.166c-048-B-B-2 | x | SELF | select 1 self | 13A.166c-048-B-B-2-1 |
| 2016-17.WN.LM8SELF | 16w.2126 | near Mostazal, CHILE | 13A.166c-048-B-B-2-1 | x | SELF | select 1 self | 13A.166c-048-B-B-2-1-2 |
| 2017.IA.INCREASE | 17s.04098 | near Kelley, IA | 13A.166c-048-B-B-2-1-2 | x | SELF | select 1 self | 13A.166c-048-B-B-2-1-2-2 |
| 2017-18.WN.LM1SELF | 17w.0108 & 0109 | near Mostazal, CHILE | 13A.166c-048-B-B-2-1-2-2 | x | SELF | begin bulking | 13A.166c-048-B-B-2-1-2-2-n |

| | NURSERY PROGRAM | Resulting pedigree | source of female | GEN harv | Other comments |
|---|---|---|---|---|---|
| | 2012.IA.MISC (Block 2) | 87-329 x 81-025 | | F1 | |
| | 2012-13.WN.JEG (Block 8) | (87-329x81-025)@1 | 2012 SN FLYX | S1 | |
| | 2013.IA.POPNS (Block 1) | (87-329x81-025)@2 | 12w.08032 | S2 | |
| | 2013-14.WN.JEG (Block 2) | (87-329x81-025)@3 | 13s.00021-048 | S3 | Also topcrossed (13w.03668) x 40-234/40-209 |
| | 2014.IA.ECQUAD (Seg4 Block) | (87-329x81-025)@4 | 13w.01596-B | S4 | In Prelim 14.143; topcrossed x 14-164 |
| | not in 2014-15 WN | | | | |
| | 2015.IA.INTERM | (87-329x81-025)@5 | 14s.07721 | S5 | In Interm 15.214; topcrossed x 14-164 |
| | not in 2015-16 WN | | | | |
| | 2016.IA.SegAS | (87-329x81-025)@6 | 15s.11553-2 | S6 | In Interm 16.282; topcrossed x 38-050 & 14-152 |
| | 2016-17.WN.LM8SELF | (87-329x81-025)@7 | 16s.05850-1 | S7 | |
| | 2017.IA.INCREASE | (87-329x81-025)@8 | 16w.2126-2 | S8 | In Interm 17.222, Adv 17.473, & Adv 17.474; multiple TC |
| | 2017-18.WN.LM1SELF | (87-329x81-025)@9 | 17s.04098-2 | S9 | |

In the winter of 2012-2013, F1 seed of the cross ('87-329'×'81-025') was selfed in a nursery near Buin, Chile. The resulting S1 seed was bulked. In the summer of 2013, plants from ('87-329'×'81-025')@1 were grown in the nursery near Kelley, IA and given the population code: 13A.166. Seeds from this cross were planted at high density, and 240 plants were self-pollinated. An S2 ear (13A.166c-048) was selected based on plant intactness, fast fall drydown, and overall ear appearance.

In the winter of 2013-14, S2 seed of 13A.166c-048 was grown in the winter nursery near Buin, Chile, where it was selfed and other plants were topcrossed to a proprietary BSSS tester. Two selfed S3 ears were selected and bulked together.

In the summer of 2014, S3 seed of 13A.166c-048-B was grown in the nursery near Kelley, IA and selfed. Two S4 ears were selected and bulked together based on plant intactness, fast fall dry-down, and overall ear appearance. Plants of 13A.166c-048-B were also topcrossed to one new tester in an isolation field grown in central Iowa. Hybrid topcross seed produced the previous winter (13A.166c-048×tester1) was grown and evaluated at three test sites in Iowa and Illinois. 14A.166c-048-B-B was selected based on the higher yield performance of the topcross hybrid (Table 2) compared to the hybrids of the parental inbreds topcrossed to the same tester.

TABLE 2

Hybrid topcross seed produced in winter 2013 (13A.166c-048 × tester1) was grown and evaluated at three test sites in Iowa and Illinois in 2014. Tester1 is '40-209' × '40-234', which is a proprietary sister cross having a B73/Other/B37 background. YLD = grain yield at harvest (bushels/acre); $H_2O$ = harvest moisture content (%); LSD = least significant difference.

|  | HYBRID | YLD | $H_2O$ |
|---|---|---|---|
|  | 87-329 × Tester1 | 189.9 | 19.79 |
|  | 13A.166c-048 × Tester1 | 192.3 | 20.44 |
|  | 81-025 × Tester1 | 183.2 | 21.25 |
|  | Avg Mean of all entries in test | 189.6 | 20.12 |
|  | # of Locations | 3 | 3 |
|  | LSD (.05) | 11.6 | 0.66 |
|  | Total Reps | 6 | 6 |
| 2014 | IA, Richland | 184.2 | 21.19 |
| 2014 | IA, Slater | 188.6 | 18.79 |
| 2014 | IL, Dawson | 196.0 | 20.39 |

In the summer of 2015, S4 seed of 14A.166c-048-B-B was grown in the nursery near Kelley, Iowa and selfed. Two S5 ears were selected based on plant intactness, fast fall dry-down, and overall ear appearance. Plants of 13A.166c-048-B-B were also topcrossed to tester2 again in an isolation field in central Iowa. Hybrid topcross seed produced the previous summer (13A.166c-048-B×tester2) was grown and evaluated at seven Iowa and Illinois test sites, and 13A.166c-048-B-B was selected based on the comparable yield performance, but lower harvest moisture and lodging of the topcross hybrid (Table 3) compared to similar hybrids.

TABLE 3

Hybrid topcross seed produced in summer 2014 (13A.166c-048-B × tester2) was grown and evaluated at seven Iowa and Illinois test sites in 2015. Tester2 is '14-164', which is a proprietary inbred having a B73/Southern/B37 background. YLD = grain yield at harvest (bushels/acre); $H_2O$ = harvest moisture content (%); SL = stalk lodging in % of plants in plot; RL = root lodging in % of plants in plot; LSD = least significant difference.

|  | HYBRID | YLD | $H_2O$ | SL | RL |
|---|---|---|---|---|---|
|  | 13A.166c-048-B × Tester2 | 199.0 | 17.4 | 13.5 | 1.2 |
|  | (14-164 × 14-152) × 81-025 | 200.5 | 18.1 | 15.5 | 3.3 |
|  | 14-025 × 87-329 | 193.6 | 19.0 | 16.4 | 8.1 |
|  | Avg Mean of all entries in test | 188.6 | 17.72 | 16.1 | 4.3 |
|  | # of Locations | 7 | 7 | 7 | 7 |
|  | LSD (.05) | 11 | 0.4 | 7.4 | 4 |
|  | Total Reps | 14 | 14 | 14 | 14 |
| 2015 | IA, Atlantic | 206.9 | 12.84 | 9.1 | 0.3 |
| 2015 | IA, Luther | 180.2 | 18.81 | 0 | 11.4 |
| 2015 | IA, Reinbeck | 176.0 | 18.52 | 43.8 | 0.1 |
| 2015 | IA, Tonica | 175.8 | 17.93 | 39.5 | 0.7 |
| 2015 | IL, Geneseo | 187.6 | 20.83 | 10.7 | 14 |
| 2015 | IL, Mt Pulaski | 199.2 | 14.94 | 9.1 | 0.4 |
| 2015 | NE, Arlington | 194.5 | 20.14 | 0.5 | 3.1 |

In the summer of 2016, S5 seed of 13A.166c-048-B-B-2 was grown in the nursery near Kelley, IA and selfed. Two S5 ears were selected from each row based on plant integrity, fast fall dry-down, and overall ear appearance. Plants of 13A.166c-048-B-B-2 were also topcrossed to two new testers. Hybrid topcross seed produced the previous summer (13A.166c-048-B-B×tester2) was grown and evaluated at 10 test sites in the Midwestern USA, and 13A.166c-048-B-B-2 was selected based on the higher yield performance and lower harvest moisture and lodging of the topcross hybrid (Table 4) compared to similar hybrids.

TABLE 4

Hybrid topcross seed produced in summer 2015 (13A.166c-048-B-B × tester2) was grown and evaluated at 10 test sites in the Midwestern USA in 2016. Tester2 is '14-164', which is a proprietary inbred having a B73/Southern/B37 background. YLD = grain yield at harvest (bushels/acre); $H_2O$ = harvest moisture content (%); SL = stalk lodging in % of plants in plot; RL = root lodging in % of plants in plot; LSD = least significant difference.

|  | HYBRID | YLD | $H_2O$ | SL | RL |
|---|---|---|---|---|---|
|  | 13A.166c-048-B-B × Tester2 | 224.0 | 16.75 | 1.4 | 5.7 |
|  | TR6254 × 81-025 | 210.9 | 16.92 | 0.4 | 7.0 |
|  | TR7443 × TR7660 | 220.2 | 17.65 | 3.2 | 10.3 |
|  | 14-025 × 81-012 | 216.9 | 17.97 | 0.4 | 10.6 |
|  | Avg Mean of all entries in test | 216.9 | 17.44 | 2.6 | 9.6 |
|  | # of Locations | 10 | 10 | 8 | 7 |
|  | LSD (.05) | 9.3 | 0.4 | 2.7 | 8.1 |
|  | Total Reps | 20 | 20 | 16 | 14 |
| 2016 | IA, Atlantic | 202.8 | 15.80 | 0.4 |  |
| 2016 | IA, Luther | 234.2 | 20.62 | 0.2 | 0.2 |
| 2016 | IA, Richland | 224.9 | 16.36 |  |  |
| 2016 | IL, Champaign | 199.0 | 15.39 | 0.1 | 46 |
| 2016 | IL, Jacksonville | 206.6 | 17.59 | 0.8 | 0.1 |
| 2016 | IL, Mt Pulaski | 217.2 | 14.02 |  |  |
| 2016 | IL, Roseville | 255.9 | 18.34 | 1.1 | 0.4 |
| 2016 | IN, Farmersberg | 208.7 | 19.31 | 4.9 | 2.8 |
| 2016 | MO, St Joseph | 204.0 | 17.75 | 10.2 | 7.9 |
| 2016 | NE, Arlington | 215.3 | 19.20 | 2.8 | 9.5 |

In the winter of 2016-2017, S6 seed of 13A.166c-048-B-B-2-1 was grown in the winter nursery near Mostazal, Chile, where it was selfed and topcrossed to multiple testers. Two selfed S7 ears were selected based on overall plant and ear appearance.

In the summer of 2017, S7 seed of 13A.166c-048-B-B-2-1-2 was grown in the nursery near Kelley, IA, and selfed. Two S7 ears were selected and bulked based on overall plant and ear appearance. Plants of 13A.166c-048-B-B-2-1-2 were also topcrossed to multiple testers. Hybrid topcross seeds produced the previous summer (13A.166c-048-B-B-2-1×2 testers) were grown and evaluated at multiple test sites, and 13A.166c-048-B-B-2-1-2-2 was selected based on the higher yield performance and lower harvest moisture of the two topcross hybrids (Tables 5 and 6) compared to similar hybrids.

TABLE 5

Hybrid topcross seeds produced in summer 2016 (13A.166c-048-B-B-2-1 × Tester3) were grown and evaluated at nine test sites in the Midwestern USA in 2017. Tester3 is a proprietary inbred having a B73/Southern/B37 background. YLD = grain yield at harvest (bushels/acre); $H_2O$ = harvest moisture content (%); SL = stalk lodging in % of plants in plot; RL = root lodging in % of plants in plot; LSD = least significant difference.

| | HYBRID | YLD | $H_2O$ | SL | RL |
|---|---|---|---|---|---|
| | 13A.166c-048-B-B-2 × Tester3 | 241.3 | 18.2 | 2.2 | 3.3 |
| | 94-016 × Tester3 | 239.7 | 18.3 | 3.0 | 0.8 |
| | 38-050 × 81-025 | 222.7 | 18.4 | 0.1 | 5.1 |
| | Tester3 × TR7987 | 236.8 | 18.7 | 2.3 | 1.3 |
| | (14-025*14-152) × 81-025 | 220.9 | 19.0 | 0.1 | 1.7 |
| | Avg Mean of all entries in test | 227.8 | 18.17 | 3.1 | 3.7 |
| | # of Locations | 9 | 9 | 9 | 9 |
| | LSD (.05) | 9.1 | 0.4 | 4.4 | 4.1 |
| | Total Reps | 18 | 18 | 18 | 18 |
| 2017 | IA, Atlantic | 240.4 | 16.27 | 18 | 2 |
| 2017 | IA, Richland | 170.5 | 15.66 | 3 | 0 |
| 2017 | IA, Slater | 243.2 | 20.95 | 0 | 2 |
| 2017 | IL, Champaign | 226.2 | 19.27 | 1 | 25 |
| 2017 | IL, Dawson | 230.5 | 18.61 | 1 | 0 |
| 2017 | IL, Jacksonville | 210 | 17.87 | 0 | 0 |
| 2017 | IL, Roseville | 256.9 | 19.2 | 0 | 1 |
| 2017 | IN, Farmersburg | 242.9 | 20.68 | 0 | 5 |
| 2017 | MO, St Joseph | 229.4 | 14.99 | 6 | 0 |

TABLE 6

Hybrid topcross seeds produced in summer 2016 (13A. 166c-048-B-B-2-1 × Tester4) were grown and evaluated at nine test sites in the Midwestern USA in 2017. Tester4 is a proprietary inbred having a B73/Other/B37 background. YLD = grain yield at harvest (bushels/acre); $H_2O$ = harvest moisture content (%); LSD = least significant difference.

| | HYBRID | YLD | $H_2O$ | SL | RL |
|---|---|---|---|---|---|
| | TR6254 × 81-025 | 221.0 | 18.02 | 0.7 | 1.7 |
| | 13A.166c-048-B-B-2 × Tester4 | 233.7 | 18.26 | 0.3 | 6.3 |
| | Tester4 × 81-025 | 221.9 | 18.33 | 1.7 | 8.4 |
| | Avg Mean of all entries in test | 227.5 | 18.45 | 1.1 | 10.4 |
| | # of Locations | 9 | 9 | 9 | 9 |
| | LSD (.05) | 10 | 0.4 | 1.6 | 6.1 |
| | Total Reps | 18 | 18 | 18 | 18 |
| 2017 | IA, Atlantic | 233.7 | 16.06 | 5 | 7 |
| 2017 | IA, Richland | 155.8 | 16.1 | 2 | 0 |
| 2017 | IA, Richland | 10.89 | 4.17 | 176 | |
| 2017 | IA, Slater | 236.7 | 20.49 | 0 | 1 |
| 2017 | IL, Champaign | 221.3 | 19.87 | 0 | 73 |
| 2017 | IL, Dawson | 236.6 | 19.51 | 1 | 6 |
| 2017 | IL, Jacksonville | 216 | 18.3 | 0 | 0 |
| 2017 | IL, Roseville | 260.8 | 20.55 | 0 | 1 |
| 2017 | IN, Farmersburg | 242.4 | 20.32 | 0 | 2 |
| 2017 | MO, St Joseph | 244.5 | 14.87 | 1 | 3 |

In the winter of 2017-2018, S8 seed of 13A.166c-048-B-B-2-1-2-2 was grown in the winter nursery near Mostazal, Chile, where it was selfed and topcrossed to multiple testers. Selfed S9 ears was bulked together and line coded as '166-048'.

In the summer of 2019, hybrid seeds produced the previous summer with inbred '166-048' crossed to commercial inbred '14-152' were grown and evaluated at 38 test sites in the Central USA. The hybrid made with '166-048' showed improved grain yield and standability (stalk lodging+root lodging) when compared to similar hybrids (Table 7).

TABLE 7

Hybrid seeds produced in summer 2018 (inbred '166-048' × inbred '14-152') were grown and evaluated at 38 test sites in the central USA in 2019. '14-152' is a proprietary commercial-status inbred having a B73/Southern/B37 background. YLD = grain yield at harvest (bushels/acre); $H_2O$ = harvest moisture content (%); SL = stalk lodging in % of plants in plot; RL = root lodging in % of plants in plot; LSD = least significant difference.

| HYBRID | YLD | $H_2O$ | SL | RL |
|---|---|---|---|---|
| 14-152 × 81-012 | 209.7 | 21.57 | 3.2 | 3.4 |
| TR7289 × TR6905 | 210.2 | 21.62 | 1.4 | 5.7 |
| 14-152 × 94-016 | 217.8 | 21.95 | 4.5 | 1.8 |
| 14-152 × 166-048 | 226.3 | 22.19 | 2.4 | 0.8 |
| 41-002 × 81-025 | 215.3 | 22.36 | 3.5 | 1.1 |
| Avg Mean of all entries in test | 217.5 | 21.8 | 3.2 | 2.9 |
| # of Locations | 38 | 38 | 38 | 38 |
| LSD (.05) | 9.0 | 0.4 | 2.7 | 3.9 |
| Total Reps | 50 | 50 | 50 | 50 |

Example 2

Description of '166-048'

In hybrid combinations, '166-048' shows higher yield and lower harvest moisture than comparable hybrids, and broad general combining ability with BSSS inbreds. An inbred description is presented in Table 8. Inbred '166-048' is compared to publicly available inbred 'PH24E' for 42 phenotypic plant characteristics.

TABLE 8

Inbred '166-048' as compared to inbred 'PH24E'.

| TRAIT | 166-048 | PH24E |
|---|---|---|
| Cob Color | Red | Red |
| Cob Diameter (mm) | 27 | 26 |
| Ear Diameter (mm) | 47 | 42 |
| Ear Length (mm) | 120 | 160 |
| Taper | Cylindrical | Semi-conical |
| Cap Color | 2.5Y 7/10 | 2.5Y 8/8 |
| Kernel Length (mm) | 10 | 14 |
| Kernel Row Direction | straight | straight |
| Kernel Row Number | 16 | 14 |
| Kernel Thickness (mm) | 5.5 | 5 |
| Kernel Type | dent | dent |
| Stalk Ear Height (cm) | 66 | 81 |
| Stalk Plant Height (cm) | 175 | 162 |
| Silk Color | Green | Pink |
| Kernel Number Per Row | 20 | 28 |
| Kernel Width (mm) | 9 | 8.25 |
| Leaf Color | 5GY 4/4 | 7.5G 4/4 |
| Leaf Length (cm) | 84 | 71 |
| Leaf Longitudinal Creases | few | few |
| Leaf Marginal Waves | few | few |
| Leaf Sheath Anthocyanin | absent | absent |
| Leaf Sheath Pubescence | light | medium |
| Leaf Width (cm) | 7 | 8 |
| Stalk Brace Root Color | Green | Purple |
| Stalk Internode Direction | ZigZag | ZigZag |
| Stalk Internode Length (cm) | 15 | 14 |
| Tassel Anther Color | 5Y 8/6 | 2.5Y 8/6 |
| Tassel Branch Number | 4 | 11 |

TABLE 8-continued

Inbred '166-048' as compared to inbred 'PH24E'.

| TRAIT | 166-048 | PH24E |
|---|---|---|
| Tassel Glume Band | absent | absent |
| Tassel Glume Color | green | green |
| Tassel Length (cm) | 33 | 39 |
| Tassel Peduncle Length | 10 | 5 |
| Pollen Shed (50%) | 1274 | 1322 |
| Silking (50%) | 1322 | 1365 |
| Leaf Angle (degree) | 30 | 25 |
| Leaf Number | 16 | 17 |
| Stalk Diameter | 20 | 21.5 |
| Stalk Nodes With Brace Roots | 2 | 2.5 |
| Stalk Tillers | 0 | 0 |
| Tassel Attitude | open | open |
| Tassel Branch Angle (degree) | 65 | 20 |
| Tassel Spike Length (cm) | 24 | 24 |

The closest comparison of inbred '166-048' to a similar inbred is with proprietary inbred '81-025'. Inbred '166-048' was derived from a cross of inbred '81-025'. '81-025' is half of the parentage of inbred '166-048'.

Figure 2:
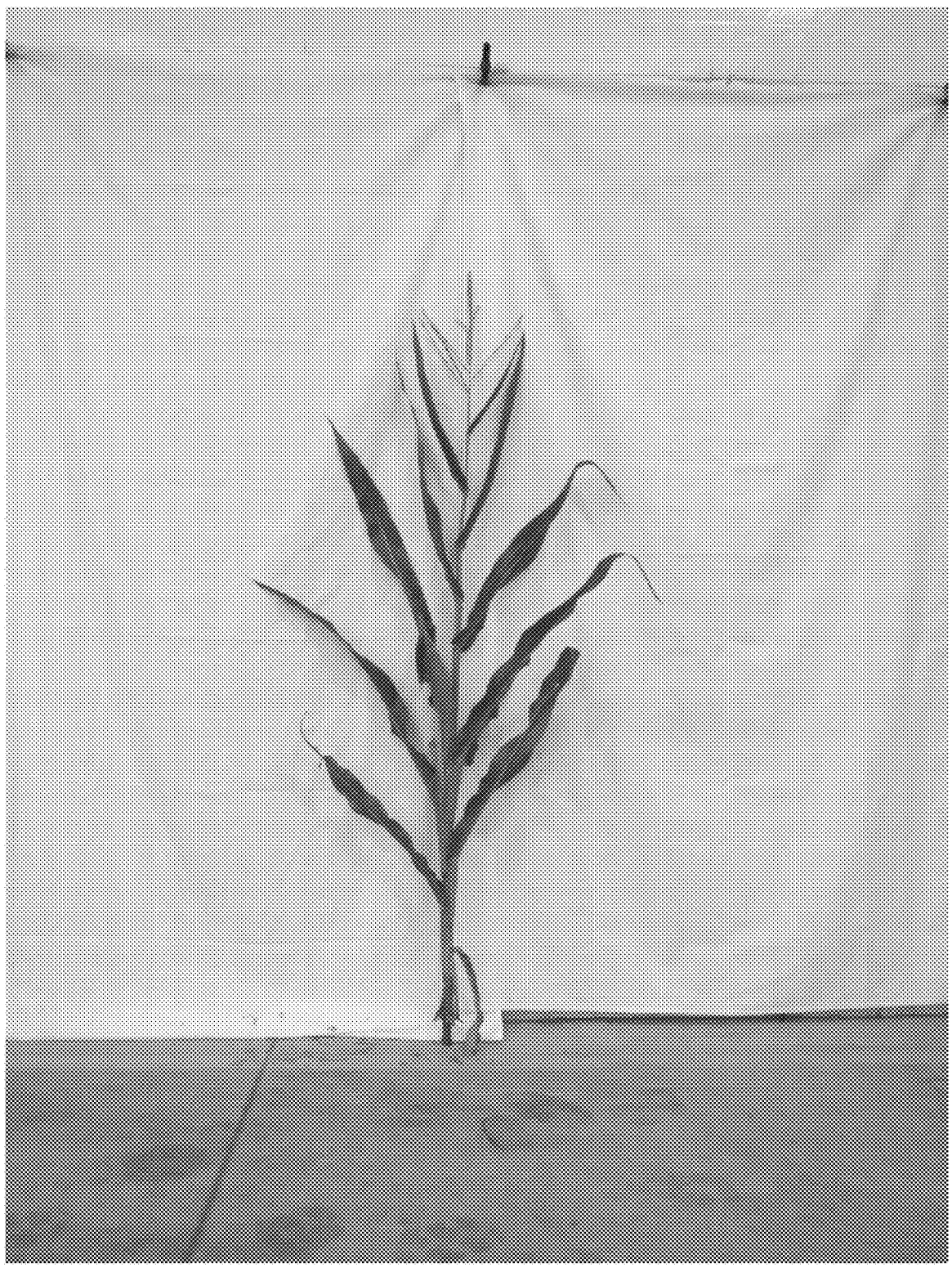
FIG. 2 shows a whole plant of corn variety '81-025'.
Figure 3:
FIG. 3 shows tassels of corn variety '166-048'.
Figure 4:
FIG. 4 shows tassels of corn variety '81-025'.
Figure 5:
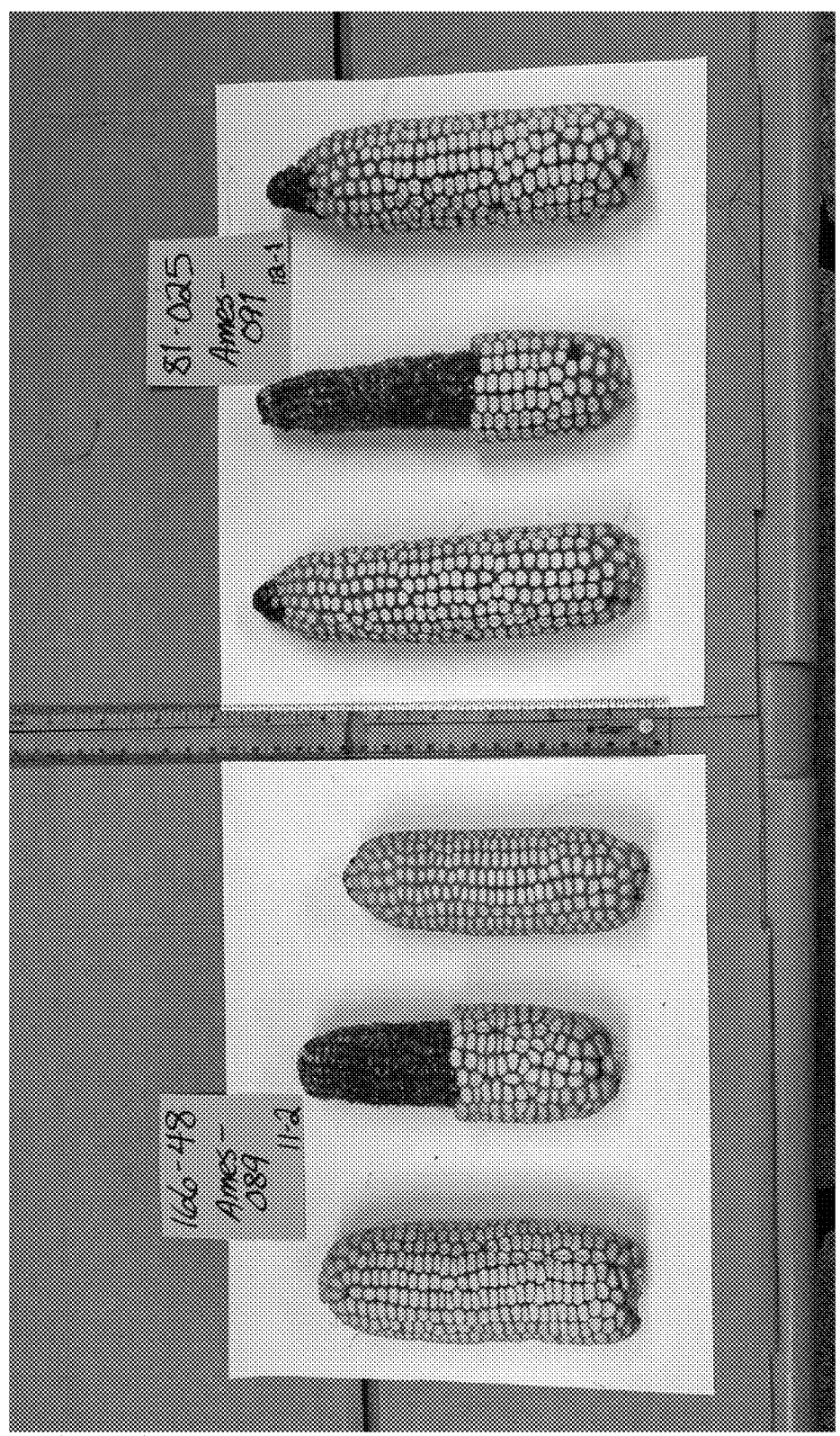
FIG. 5 shows ears from corn varieties '166-048 (left) and '81-025' (right).

Inbred '166-048' has longer leaves and a more conventional leaf orientation when compared to inbred '81-025', which has shorter, more upright leaves (FIGS. 1 & 2). The two inbreds have similar tassel appearances but inbred '166-048' generally has fewer tassel branches (FIGS. 3 & 4). Inbred '166-048' has a slightly shorter, girthier ear, and slightly smaller kernels in comparison with inbred '81-025' (FIG. 5; Table 9).

TABLE 9

Inbred '166-048' has a slightly shorter, girthier ear, and slightly smaller kernels as compared to inbred '81-025'. Observations are based on 10 OP ears collected from a nursery where both inbreds were grown in 2020.

| TRAIT | 166-48 | 81-025 |
|---|---|---|
| Cob Color | Red | Red |
| Cob Diameter (mm) | 33-35 | 27-29 |
| Cob Circumference (mm) | 110-114 | 93-97 |
| Ear Diameter (mm) | 48-52 | 38-42 |
| Ear Length (mm) | 127-136 | 152-160 |
| Taper | Cylindrical | Cylindrical |
| Kernel Length (mm) | 9-11 | 11-13 |
| Kernel Row Direction | straight | straight |
| Kernel Row Number | 18-20 | 18-20 |
| Kernel Thickness (mm) | 4.0-4.5 | 4.5-5.0 |
| Kernel Type | dent | dent |

In direct hybrid comparisons, inbred '166-048' produces higher yields and has a lower harvest moisture level when compared to similar '81-025' hybrids (i.e., when both inbreds are crossed to the same inbred) (Table 10).

TABLE 10

In direct hybrid comparisons, inbred '166-048' produced higher yields and had a lower harvest moisture level as compared to similar '81-025' hybrids (i.e. when both inbreds were crossed to the same inbred). YLD = grain yield at harvest (bushels/acre); H$_2$O = harvest moisture content (%); SL = stalk lodging in % of plants in plot; RL = root lodging in % of plants in plot; CVErr = test error estimate; LSD = least significant difference.

| HYBRID | YLD | H$_2$O | SL | RL |
|---|---|---|---|---|
| 106-43 × 166c-048 | 215.5 | 20.64 | 0.8 | 0.4 |
| 106-43 × 81-025 | 203.0 | 20.97 | 3.0 | 0.3 |

TABLE 10-continued

In direct hybrid comparisons, inbred '166-048' produced higher yields and had a lower harvest moisture level as compared to similar '81-025' hybrids (i.e. when both inbreds were crossed to the same inbred). YLD = grain yield at harvest (bushels/acre); H$_2$O = harvest moisture content (%); SL = stalk lodging in % of plants in plot; RL = root lodging in % of plants in plot; CVErr = test error estimate; LSD = least significant difference.

| HYBRID | YLD | H$_2$O | SL | RL |
|---|---|---|---|---|
| Avg Mean of all entries in test | 210.2 | 20.6 | 1.8 | 1.1 |
| # of Locations | 26 | 26 | 26 | 26 |
| CVErr | 5.1 | 2.8 | 104.6 | 217.3 |
| LSD (.05) | 10.4 | 0.5 | 2.4 | 2.6 |
| Total Reps | 48 | 48 | 48 | 48 |

Example 3

Production of '166-048' Corn

'166-048' can be grown under normal conditions for growing corn, and bulk seed for large-scale planting can be obtained by methods known in certified seed production. For example, bulk seed may be produced by planting '166-048' seeds (such as those obtained from ATCC Accession No: PTA-127596), allowing the mature plants to produce seed by self-pollination with each other and then collecting the seed. Standard precautions can be taken to prevent cross-pollination from other corn, such as growing the variety in an isolated plot of sterilized soil, removing adjacent vegetation, etc. The '166-048' seeds deposited with ATCC are breeder seeds; propagation of plants from these seeds can be performed under standard conditions.

Example 4

Introducing Traits of '166-048' into Other Corn Varieties

The morphological and physiological characteristics of '166-048', including higher yield and lower harvest moisture than comparable hybrids and broad general combining ability with BSSS inbreds, can be introduced into other corn varieties (such as other corn cultivars) by conventional breeding techniques. For example, '166-048' can be grown in pollination proximity to another variety of corn, allowing cross-pollination to occur between '166-048' and the other variety, and then harvesting the hybrid seeds. Plants grown from these hybrid seeds can then be tested for the maintenance of the characteristics described herein for '166-048' (such as one or more of higher yield and lower harvest moisture than comparable hybrids, and broad general combining ability with BSSS inbreds), and/or the plants can simply be observed to see if they display the same characteristics described in Tables 7-10.

For example, plants grown from these hybrid seeds can be tested for any of the morphological characteristics described herein. In this way, higher yield and lower harvest moisture than comparable hybrids and broad general combining ability with BSSS inbreds may be combined with other desirable plant characteristics. Thus, the provision of '166-048' enables the production of progeny plants of '166-048' having one or more of higher yield and/or lower harvest moisture than comparable hybrids, and broad general combining ability with BSSS inbreds, and in some examples all of these, and in some examples also additional traits, such as pest resistance. "Progeny plants" of '166-048' are any plants that are the offspring of a cross between '166-048' and any other plant or plants. Progeny plants also include successive generations of the offspring, for example those selected for yield and/or harvest moisture content. First-generation progeny plants may retain the seed yield and/or harvest moisture content phenotypes of the '166-048' parent. However, if a first-generation progeny plant does not retain one or more of these phenotypes observed with '166-048', subsequent generations of offspring can be recycled. In one embodiment, subsequent generations of offspring can have seed yields and/or harvest moisture contents similar to that or even improved over that of '166-048'.

In addition, '166-048' can be used as a transformation targets for producing transgenic corn. In certain embodiments, the present disclosure contemplates the transformation of cells derived from '166-048' with at least one transgene. For example, transgenes that can be used, include, but are not limited to, transgenes that confer resistance to one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, and modified corn fiber characteristics. Examples of such genes and methods of transforming plants are described in U.S. Pat. No. 6,025,545.

Example 5

Genotyping and Genetic Marker Profile of '166-048'

The disclosure is not limited to particular methods of determining the genotype of a corn plant, such as '166-048' or a plant derived therefrom. In one example, isozymes are used to provide a generalized footprint of the genetic material. Other exemplary methods include restriction fragment length polymorphisms (RFLPs), amplified fragment length polymorphisms (AFLPs), random amplified polymorphic DNAs (RAPDs), amplification methods such as the polymerase chain reaction (PCR), which can employ different types of primers or probes, microsatellites (SSRs), single nucleotide polymorphisms (SNPs), sequence selection markers, and the like.

The marker profile of a corn plant provided herein can be close to homozygous for alleles. A marker profile produced with any of the locus identifying systems known in the industry will identify a particular allele at a particular locus. An F1 hybrid made from '166-048' can include a marker profile of the sum of both of the profiles of its inbred parents. At each locus, the allele for '166-048' and the allele for the other inbred parent should be present. Thus the profile of '166-048' allows for identification of hybrids as containing the parent of '166-048'. To identify the female portion of any hybrid, the hybrid seed material from the pericarp, which is maternally inherited, is employed in a marker technique. The resultant profile, therefore, is of the maternal parent. A comparison of this maternal profile with the hybrid profile allows for the identification of the paternal profile. Accordingly, in some examples, provided herein is an inbred or hybrid plant, plant part thereof, including but not limited to a seed or an embryo, and/or a cell thereof having the allele marker profile of '166-048'.

Marker profiles of plants provided herein can be employed to identify essentially derived varieties or progeny developed with '166-048' in its ancestry. The progeny of '166-048', can be identified by identifying in the progeny the molecular marker profile of '166-048', as measured by either percent identity or percent similarity.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Therefore, as used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

Marker systems can be used to identify plants provided herein and for breeding and trait conversion techniques. Polymorphisms in corn permit the use of markers for linkage analysis. If SSR are employed with flanking primers, the marker profile can be developed with PCR, and Southern blots can often be eliminated. Primer sequences for SSR markers and maize genome mapping information are publicly available on the USDA website at the Maize Genomics and Genetic Database (Maize GDB).

Example 7

Producing Treated Corn Seed

Methods are provided for producing treated hybrid or inbred seed of '166-048' plants and the resultant treated seed. Such a method can include obtaining seed and treating the seed to improve its performance. For example, seed provided herein can be treated with one or more of: fungicides, herbicides, herbicidal safeners, fertilizers, insecticides, acaricides, nematocides, bactericides, virus resistant material and/or other biocontrol agents. In one example, seed provided herein can be treated with one or more of: pyrethrins, synthetic pyrethroids, oxadizine derivatives, chloronicotinyls, nitroguanidine derivatives and triazoles, organophosphates, pyrrols, pyrazoles, phenyl pyrazoles, diacylhydrazines, biological/fermentation products, carbamates and the like are used as pesticidal seed treatments. In one example, seed provided herein can be treated with one or more of: fludioxonil, mefenoxam, azoxystrobin, thiamethoxam, clothianidin and the like. Methods for treating seed include the use of a fluidized bed, a roller mill, a rotostatic seed treater. a drum coaster, misting, soaking, filming coating and the like, in any combination.

Example 8

Corn Commodity Products

The present disclosure provides commodity products produced from '166-048' corn plants and seeds provided herein, including plants bred from '166-048' and resulting seed.

In one example, the methods of producing a commodity plant product includes obtaining a '166-048 corn plant, or a part thereof comprising a cell of corn variety '166-048', and producing the commodity plant product therefrom. In one example, the methods include planting seeds provided herein, growing plant from such seeds, harvesting the plants and/or processing them to obtain an agricultural or industrial product. In some examples, the method of producing a commodity corn product includes growing the plant from a seed provided herein or a part thereof and producing said commodity plant product. Exemplary commodity plant products include a protein concentrate, protein isolate, starch, corn syrup, flour, grain, meal, or oil.

The food uses of corn, in addition to human consumption of corn kernels, include both products of dry- and wet-milling industries. Exemplary products of corn dry milling are grits, meal and flour. Exemplary products of corn wet-milling include corn starch, corn syrups and dextrose for food use. Corn oil can be recovered from maize germ, a by-product of both dry- and wet-milling industries.

In one example, the segregating grain formed on the ear of the plant is a commodity corn product as are the protein concentrate, protein isolate, starch, meal, flour or oil.

Grain and non-grain portions of the corn plant can be used livestock feed, for example for beef cattle, dairy cattle, hogs, and poultry. Industrial uses of corn include production of ethanol, corn starch in the wet-milling industry and corn flour in the dry-milling industry.

In one example, the corn commodity product includes stalks and husks, which can be made into paper and wallboard. In one example, the corn commodity product includes cobs, which can be used for fuel and to make charcoal.

In some examples, the commodity product includes a cell of corn variety '166-048'.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A seed of corn variety '166-048', wherein a representative sample of seed of the variety has been deposited under American Type Culture Collection (ATCC) Accession No: PTA-127596.

2. A seed mixture, comprising the seed of claim 1.

3. A corn plant of corn variety '166-048' grown from the seed of claim 1.

4. A plant part of the corn plant of claim 3.

5. The plant part of claim 4, wherein the plant part is a pollen grain, a silk, a protoplast, a cell, a tassel, an anther or an ovule.

6. A tissue culture produced from protoplasts or cells from the corn plant of claim 3.

7. The tissue culture of claim 6, wherein the cells or protoplasts are produced from an embryo, ovule, meristematic cell, pollen, leaf, roots root tip, anther, pistil, silk, flower, kernel, ear, cob, husk, seed, cotyledon, hypocotyl, shoot, and/or stem.

8. A corn plant regenerated from the tissue culture of claim 7, wherein the corn plant comprises all of the morphological and physiological properties of a corn plant grown from a seed deposited under ATCC Accession No: PTA-127596.

9. A composition comprising the seed of claim 1 comprised in plant seed growth media.

10. The composition of claim 9, wherein the growth media is soil or a synthetic cultivation medium.

11. The seed of claim 1, further comprising a single transgene, wherein said transgene is introduced by backcrossing or genetic transformation into corn variety '166-048'.

12. The seed of claim 11, wherein the transgene confers one or more of herbicide tolerance, resistance to a bacterial disease, resistance to a viral disease, resistance to a fungal disease, resistance to a nematode, resistance to an insect, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, waxy starch, modified phytic acid metabolism, modified protein metabolism, water stress resistance, restoration of male fertility, altered starch, thermotolerant amylase, and modified corn fiber characteristics.

13. The plant of claim 3, further comprising a transgene, wherein said transgene is introduced by backcrossing or genetic transformation into corn variety '166-048'.

14. The plant of claim 13, wherein the transgene confers one or more of herbicide tolerance, resistance to a bacterial disease, resistance to a viral disease, resistance to a fungal disease, resistance to a nematode, resistance to an insect, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, waxy starch, modified phytic acid metabolism, modified protein metabolism, water stress resistance, restoration of male fertility, altered starch, thermotolerant amylase, and modified corn fiber characteristics.

15. A corn seed comprising a single locus conversion, wherein the single locus conversion is introduced by backcrossing or genetic transformation into corn variety '166-048' wherein representative seeds of variety '166-048' is deposited under ATCC Accession No: PTA-127596.

16. A corn plant comprising a single locus conversion, wherein the single locus conversion is introduced by backcrossing or genetic transformation into corn variety '166-048', and wherein representative seeds of variety '166-048' is deposited under ATCC Accession No: PTA-127596.

17. A method of producing corn seed, comprising:
crossing the corn plant of claim 3 with itself or a second corn plant; and
harvesting a resulting corn seed.

18. A corn seed produced by the method of claim 17.

19. A corn plant, or a part thereof, produced by growing the seed of claim 18.

20. The method of claim 17, wherein the second corn plant is transgenic.

21. An $F_1$ hybrid seed produced by the method of claim 18.

22. A method of producing a corn plant, comprising:
transforming a transgene conferring an additional trait into the corn plant of claim 3, thereby producing a corn plant comprising the added trait.

23. The method of claim 22, wherein the additional trait is one or more of herbicide tolerance, resistance to a bacterial disease, resistance to a viral disease, resistance to a fungal disease, resistance to a nematode, resistance to an insect, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, waxy starch, modified phytic acid metabolism, modified protein metabolism, water stress resistance, restoration of male fertility, altered starch, thermotolerant amylase, and modified corn fiber characteristics.

24. The method of claim 22, wherein the transgene encodes phytase, fructosyltransferase, levansucrase, α-amylase, invertase, or stearoyl-acyl carrier protein (ACP) desaturase.

25. The method of claim 23, wherein the resistance to an insect is conferred by a transgene encoding a *Bacillus thuringiensis* (Bt) endotoxin.

26. The method of claim 23, wherein the herbicide tolerance comprises tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, and chlorophenoxy acetic acid.

27. A corn plant produced by the method of claim 22.

28. A method of introducing an additional trait into corn variety '166-048' comprising:
(a) crossing the corn plant of claim 3 with another corn plant comprising an additional trait to produce $F_1$ progeny plants;
(b) selecting $F_1$ progeny plants that have the additional trait to produce selected $F_1$ progeny plants;
(c) crossing the selected $F_1$ progeny plants with at least one plant of variety '166-048' to produce backcross progeny plants;
(d) selecting backcross progeny plants that have the additional trait and physiological and morphological characteristics of corn variety '166-048' to produce selected backcross progeny plants; and
(e) repeating steps (c) and (d) one or more times in succession to produce selected second or higher backcross progeny plants that comprise the additional trait and the physiological and morphological characteristics of corn variety '166-048' when grown in the same environmental conditions.

29. The method of claim 28, wherein the additional trait comprises one or more of herbicide tolerance, resistance to a bacterial disease, resistance to a viral disease, resistance to a fungal disease, resistance to a nematode, resistance to an insect, resistance to a pest, male sterility, site-specific recombination, abiotic stress tolerance, modified phosphorus characteristics, modified antioxidant characteristics, modified essential seed amino acid characteristics, modified fatty acid metabolism, modified carbohydrate metabolism, waxy starch, modified phytic acid metabolism, modified protein metabolism, water stress resistance, restoration of male fertility, altered starch, thermotolerant amylase, and modified corn fiber characteristics.

30. A method of producing a progeny corn plant derived from corn variety '166-048', wherein the method comprises applying plant breeding techniques to the corn plant of claim 3 to produce the progeny corn plant derived from corn variety '166-048'.

31. The method of claim 30, wherein said plant breeding techniques comprise recurrent selection, mass selection, bulk selection, backcrossing, marker assisted breeding, pedigree breeding, selfing, outcrossing, haploid production, doubled haploid production, or genetic transformation.

32. The method of claim 30, further comprising:
(a) crossing the progeny corn plant derived from hybrid corn variety '166-048' with itself or a second plant to produce a seed of a progeny plant of a subsequent generation;
(b) growing the progeny plant of the subsequent generation from said seed of the progeny plant of the subsequent generation; and
(c) repeating steps (a) and (b) for at least an additional generation to produce a progeny corn plant further derived from the corn variety '166-048'.

33. A method of producing a hybrid corn plant derived from corn variety '166-048', comprising:
(a) preparing a progeny plant derived from corn variety '166-048' by crossing the corn plant of claim 3 with a corn plant of a second variety;
(b) crossing the progeny plant with itself or a second plant to produce a seed of a progeny plant of a subsequent generation;
(c) growing a progeny plant of the subsequent generation from said seed and crossing the progeny plant of the subsequent generation with itself or a second plant; and
(d) repeating steps (b) and (c) for at least an additional generation with sufficient inbreeding to produce a hybrid corn plant derived from the corn variety '166-048'.

34. A plant produced by the method of claim 28 having all of the physiological and morphological characteristics of corn variety '166-048'.

35. A method of producing a commodity plant product comprising:
obtaining the corn plant of claim 3 or a part thereof; and producing the commodity plant product therefrom.

36. The method of claim 35, wherein the commodity plant product is protein concentrate, protein isolate, starch, corn syrup, flour, grain, meal, or oil.

37. A process for producing corn seed, comprising:
crossing the corn plant of claim 3 with a different corn plant; and
harvesting the seed.

38. An F1 corn seed produced by the process of claim 37.

39. An F1 corn plant produced by germinating the seed of claim 38.

40. A method of producing a corn plant with doubled haploid chromosomes from corn variety '166-048', comprising:
(a) crossing the corn plant of claim 39 with an inducer corn plant to produce a progeny with haploid chromosomes; and
(b) doubling the haploid chromosomes in the progeny to produce a corn plant with doubled haploid chromosomes.

41. A method of producing a genetic marker profile, comprising:
extracting nucleic acids from the seed of claim 38 or the plant germinated from said seed and genotyping said nucleic acids at one or more genetic loci, thereby producing a genetic marker profile.

42. A method of plant breeding, comprising
isolating nucleic acids from the seed of claim 38;
identifying one or more polymorphisms from the isolated nucleic acids; and
selecting a plant obtained from said seed having said one or more polymorphisms, wherein the plant is used in a plant breeding method.

43. A method of plant breeding, comprising:
isolating nucleic acids from the plant of claim 39;
identifying one or more polymorphisms from the isolated nucleic acids; and
selecting a plant having said one or more polymorphisms, wherein the plant is used in a plant breeding method.

\* \* \* \* \*